(12) United States Patent
Bender et al.

(10) Patent No.: US 7,794,471 B1
(45) Date of Patent: Sep. 14, 2010

(54) COMPLIANT ANASTOMOSIS SYSTEM

(75) Inventors: Theodore M. Bender, San Francisco, CA (US); Luke W. Clauson, Redwood Shores, CA (US); Philipe R. Manoux, San Francisco, CA (US); Zachary Warder-Gabaldon, Palo Alto, CA (US); Tenny Chang, Mountain View, CA (US); Kathleen H. Davies, Fremont, CA (US); Stephen A. Yencho, Menlo Park, CA (US); Brian R. DuBois, Redwood City, CA (US); Bernard A. Hausen, Menlo Park, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 1258 days.

(21) Appl. No.: 10/877,971

(22) Filed: Jun. 25, 2004

Related U.S. Application Data

(60) Provisional application No. 60/483,079, filed on Jun. 26, 2003.

(51) Int. Cl.
*A61B 17/11* (2006.01)
(52) U.S. Cl. .................. 606/153; 606/142
(58) Field of Classification Search ......... 606/139–146, 606/151, 153, 154, 167–185; 227/175.1, 227/175.2, 180.1, 181.1; 408/68, 127, 208, 408/209; 74/56–58, 63–69
See application file for complete search history.

(56) References Cited

U.S. PATENT DOCUMENTS

| | | | |
|---|---|---|---|
| 2,012,776 A | 8/1935 | Roeder | |
| 2,566,625 A | 9/1951 | Nagelmann | |
| 3,090,386 A | 5/1963 | Curtis | |
| 3,177,021 A | 4/1965 | Benham | |
| 3,254,650 A | 6/1966 | Collito | |
| 3,254,651 A | 6/1966 | Collito | |
| 3,344,790 A | 10/1967 | Donner | |

(Continued)

FOREIGN PATENT DOCUMENTS

DE 19732234 1/1999

(Continued)

OTHER PUBLICATIONS

Martens, et al., "The Heartflo Device for Distal Coronary Anastmosis: Clinical Experiences in 60 Patents", Annals for Thoracic Surgery vol. 74,(2002),1139-1143.

(Continued)

*Primary Examiner*—Anhtuan T Nguyen
*Assistant Examiner*—Kathleen Sonnett
(74) *Attorney, Agent, or Firm*—Brian A. Schar

(57) ABSTRACT

An integrated anastomosis tool may include an effector that both makes an opening in the wall of a target vessel and connects a graft vessel to the target vessel. The connection between the graft vessel and the target vessel may be compliant, and may be achieved by deploying a plurality of connectors such as staples into tissue. The effector may include a cutter assembly and a connection module that are independently actuatable. The cutter assembly and/or the connection module may be cable-actuated.

22 Claims, 15 Drawing Sheets

U.S. PATENT DOCUMENTS

| | | |
|---|---|---|
| 3,519,187 A | 7/1970 | Kapitanov et al. |
| 3,643,851 A | 2/1972 | Green et al. |
| 3,647,310 A * | 3/1972 | Morse .................... 408/239 R |
| 3,662,939 A | 5/1972 | Bryan |
| 3,774,615 A | 11/1973 | Lim et al. |
| 3,788,303 A * | 1/1974 | Hall ............................ 600/148 |
| 3,871,379 A | 3/1975 | Clarke |
| 4,014,492 A | 3/1977 | Rothfuss |
| 4,018,228 A | 4/1977 | Goosen |
| 4,109,844 A | 8/1978 | Becht |
| 4,127,227 A | 11/1978 | Green |
| 4,180,196 A | 12/1979 | Hueil et al. |
| 4,214,587 A | 7/1980 | Sakura, Jr. |
| 4,256,251 A | 3/1981 | Moshofsky |
| 4,317,451 A | 3/1982 | Cerwin et al. |
| 4,331,277 A | 5/1982 | Green |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,406,392 A | 9/1983 | Campbell et al. |
| 4,410,125 A | 10/1983 | Noiles et al. |
| 4,411,378 A | 10/1983 | Warman |
| 4,493,322 A | 1/1985 | Becht |
| 4,493,323 A | 1/1985 | Albright et al. |
| 4,503,568 A | 3/1985 | Madras |
| 4,505,273 A | 3/1985 | Braun et al. |
| 4,523,592 A | 6/1985 | Daniel |
| 4,523,707 A | 6/1985 | Blake, III et al. |
| 4,553,542 A | 11/1985 | Schenck et al. |
| 4,558,810 A | 12/1985 | Mulhauser et al. |
| 4,593,693 A | 6/1986 | Schenck |
| 4,596,350 A | 6/1986 | Smith et al. |
| 4,597,390 A | 7/1986 | Mulhollan et al. |
| 4,603,693 A | 8/1986 | Conta et al. |
| 4,607,637 A | 8/1986 | Berggren et al. |
| 4,619,262 A | 10/1986 | Taylor |
| 4,624,255 A | 11/1986 | Schenck et al. |
| 4,624,257 A | 11/1986 | Berggren et al. |
| 4,634,035 A | 1/1987 | Li et al. |
| 4,645,111 A | 2/1987 | Larrabee et al. |
| 4,657,019 A | 4/1987 | Walsh et al. |
| 4,665,906 A | 5/1987 | Jervis |
| 4,671,279 A | 6/1987 | Hill |
| 4,691,853 A | 9/1987 | Storace |
| 4,741,336 A | 5/1988 | Failla et al. |
| 4,747,407 A | 5/1988 | Liu et al. |
| 4,747,531 A | 5/1988 | Brinkerhoff et al. |
| 4,752,024 A | 6/1988 | Green et al. |
| 4,760,848 A | 8/1988 | Hasson |
| 4,773,420 A | 9/1988 | Green |
| 4,776,506 A * | 10/1988 | Green .......................... 227/19 |
| 4,807,628 A | 2/1989 | Peters et al. |
| 4,811,886 A | 3/1989 | Murray |
| 4,887,756 A | 12/1989 | Puchy |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,945,920 A | 8/1990 | Clossick |
| 4,951,860 A | 8/1990 | Peters et al. |
| 5,005,749 A | 4/1991 | Aranyi |
| 5,015,250 A | 5/1991 | Foster |
| 5,037,433 A | 8/1991 | Wilk et al. |
| 5,049,153 A * | 9/1991 | Nakao et al. ................ 606/151 |
| 5,062,842 A | 11/1991 | Tiffany |
| 5,104,025 A | 4/1992 | Main et al. |
| 5,105,672 A * | 4/1992 | Carson et al. ............. 74/89.22 |
| 5,119,983 A | 6/1992 | Green et al. |
| 5,125,553 A | 6/1992 | Oddsen et al. |
| 5,129,912 A | 7/1992 | Noda et al. |
| 5,147,373 A | 9/1992 | Ferzli |
| 5,156,619 A | 10/1992 | Ehrenfeld |
| 5,176,691 A | 1/1993 | Pierce |
| 5,178,634 A | 1/1993 | Ramos Martinez |
| 5,193,731 A | 3/1993 | Aranyi |
| 5,205,459 A | 4/1993 | Brinkerhoff et al. |
| 5,211,683 A | 5/1993 | Maginot |
| 5,217,470 A | 6/1993 | Weston |
| 5,220,928 A | 6/1993 | Oddsen et al. |
| 5,234,447 A | 8/1993 | Kaster et al. |
| 5,240,164 A | 8/1993 | Murray et al. |
| 5,250,058 A | 10/1993 | Miller et al. |
| 5,251,801 A | 10/1993 | Ruckdeschel et al. |
| 5,271,544 A | 12/1993 | Fox et al. |
| 5,273,545 A | 12/1993 | Hunt et al. |
| 5,275,322 A | 1/1994 | Brinkerhoff et al. |
| 5,275,611 A | 1/1994 | Behl |
| 5,279,067 A | 1/1994 | Tollison |
| 5,285,945 A | 2/1994 | Brinkerhoff et al. |
| 5,292,053 A | 3/1994 | Bilotti et al. |
| 5,292,327 A | 3/1994 | Dodd et al. |
| 5,304,220 A | 4/1994 | Maginot |
| 5,312,023 A * | 5/1994 | Green et al. ............. 227/175.1 |
| 5,312,360 A | 5/1994 | Behl |
| 5,314,435 A | 5/1994 | Green et al. |
| 5,314,468 A | 5/1994 | Ramos Martinez |
| 5,320,629 A | 6/1994 | Noda et al. |
| 5,320,632 A | 6/1994 | Heidmueller |
| 5,333,773 A | 8/1994 | Main et al. |
| 5,336,233 A | 8/1994 | Chen |
| 5,350,104 A | 9/1994 | Main et al. |
| 5,366,462 A | 11/1994 | Kaster et al. |
| 5,366,479 A | 11/1994 | McGarry et al. |
| 5,368,601 A | 11/1994 | Sauer |
| 5,392,979 A | 2/1995 | Green et al. |
| 5,395,030 A | 3/1995 | Kuramoto et al. |
| 5,403,327 A | 4/1995 | Thornton et al. |
| 5,403,329 A | 4/1995 | Hinchcliffe |
| 5,405,352 A | 4/1995 | Weston |
| 5,417,361 A | 5/1995 | Williamson, IV |
| 5,417,699 A | 5/1995 | Klein et al. |
| 5,425,489 A | 6/1995 | Shichman et al. |
| 5,431,666 A | 7/1995 | Sauer et al. |
| 5,443,497 A | 8/1995 | Venbrux |
| 5,447,514 A | 9/1995 | Gerry et al. |
| 5,452,836 A | 9/1995 | Huitema et al. |
| 5,454,820 A | 10/1995 | Kammerer et al. |
| 5,454,825 A | 10/1995 | Van Leeuwen |
| 5,456,400 A | 10/1995 | Shichman et al. |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,344 A | 12/1995 | Stone et al. |
| 5,478,354 A | 12/1995 | Tovey et al. |
| 5,480,406 A | 1/1996 | Nolan et al. |
| 5,507,757 A | 4/1996 | Sauer et al. |
| 5,522,834 A | 6/1996 | Fonger et al. |
| 5,527,320 A | 6/1996 | Carruthers et al. |
| 5,527,322 A | 6/1996 | Klein et al. |
| 5,533,661 A | 7/1996 | Main et al. |
| 5,535,935 A | 7/1996 | Vidal et al. |
| 5,554,162 A | 9/1996 | Delange |
| 5,558,667 A | 9/1996 | Yarborough et al. |
| 5,562,241 A | 10/1996 | Knodel et al. |
| 5,562,684 A | 10/1996 | Kammerer |
| 5,571,090 A | 11/1996 | Sherts |
| 5,571,167 A | 11/1996 | Maginot |
| 5,573,286 A | 11/1996 | Rogozinski |
| 5,578,044 A | 11/1996 | Gordon et al. |
| 5,580,067 A | 12/1996 | Hamblin et al. |
| 5,586,711 A | 12/1996 | Plyley et al. |

| Patent | Date | Inventor |
|---|---|---|
| 5,591,177 A | 1/1997 | Lehrer |
| 5,609,285 A | 3/1997 | Grant et al. |
| 5,613,974 A | 3/1997 | Andreas et al. |
| 5,626,588 A | 5/1997 | Sauer et al. |
| 5,632,432 A | 5/1997 | Schulze et al. |
| 5,632,433 A | 5/1997 | Grant et al. |
| 5,634,930 A | 6/1997 | Thornton et al. |
| 5,643,293 A | 7/1997 | Kogasaka et al. |
| 5,643,340 A | 7/1997 | Nunokawa |
| 5,645,567 A | 7/1997 | Crainich |
| 5,653,373 A | 8/1997 | Green et al. |
| 5,653,719 A | 8/1997 | Raiken |
| 5,662,258 A | 9/1997 | Knodel et al. |
| 5,662,664 A | 9/1997 | Gordon et al. |
| 5,669,544 A | 9/1997 | Schulze et al. |
| 5,669,918 A | 9/1997 | Balazs et al. |
| 5,676,670 A | 10/1997 | Kim |
| 5,693,088 A | 12/1997 | Lazarus |
| 5,695,504 A * | 12/1997 | Gifford et al. ............... 606/153 |
| 5,702,412 A * | 12/1997 | Popov et al. ................ 606/159 |
| 5,707,362 A | 1/1998 | Yoon |
| 5,707,380 A * | 1/1998 | Hinchliffe et al. ........... 606/153 |
| 5,709,693 A | 1/1998 | Taylor |
| 5,709,694 A | 1/1998 | Greenberg et al. |
| 5,725,544 A | 3/1998 | Rygaard |
| 5,728,109 A | 3/1998 | Schulze |
| 5,728,113 A | 3/1998 | Sherts |
| 5,738,474 A | 4/1998 | Blewett |
| 5,746,752 A | 5/1998 | Burkhart |
| 5,759,189 A | 6/1998 | Ferragamo et al. |
| 5,769,862 A | 6/1998 | Kammerer et al. |
| 5,769,863 A | 6/1998 | Garrison |
| 5,779,719 A | 7/1998 | Klein et al. |
| 5,792,159 A | 8/1998 | Klein et al. |
| 5,797,920 A | 8/1998 | Kim |
| 5,797,929 A | 8/1998 | Andreas et al. |
| 5,799,857 A | 9/1998 | Robertson et al. |
| 5,810,852 A | 9/1998 | Greenberg et al. |
| 5,817,113 A | 10/1998 | Gifford, III et al. |
| 5,833,698 A | 11/1998 | Hinchliffe et al. |
| 5,865,730 A | 2/1999 | Fox et al. |
| 5,868,760 A * | 2/1999 | McGuckin, Jr. ............. 606/139 |
| 5,879,371 A | 3/1999 | Gardiner et al. |
| 5,897,563 A | 4/1999 | Yoon et al. |
| 5,902,311 A | 5/1999 | Andreas et al. |
| 5,915,616 A | 6/1999 | Viola et al. |
| 5,921,994 A | 7/1999 | Andreas et al. |
| 5,921,995 A | 7/1999 | Kleshinski |
| 5,938,101 A | 8/1999 | Izuchukwu et al. |
| 5,944,730 A | 8/1999 | Nobles et al. |
| 5,976,159 A | 11/1999 | Bolduc et al. |
| 5,993,464 A | 11/1999 | Knodel |
| 6,015,416 A | 1/2000 | Stefanchik et al. |
| 6,024,748 A | 2/2000 | Manzo et al. |
| 6,036,699 A | 3/2000 | Andreas et al. |
| 6,036,700 A | 3/2000 | Stefanchik et al. |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,071,289 A | 6/2000 | Stefanchik et al. |
| 6,083,234 A | 7/2000 | Nicholas et al. |
| 6,110,187 A | 8/2000 | Donlon |
| 6,117,144 A | 9/2000 | Nobles et al. |
| 6,117,148 A | 9/2000 | Ravo et al. |
| 6,132,439 A | 10/2000 | Kontos |
| 6,136,010 A | 10/2000 | Modesitt et al. |
| 6,171,317 B1 | 1/2001 | Jackson et al. |
| 6,176,413 B1 | 1/2001 | Heck et al. |
| 6,183,486 B1 | 2/2001 | Snow et al. |
| 6,187,019 B1 | 2/2001 | Stefanchik et al. |
| 6,190,396 B1 | 2/2001 | Whitin et al. |
| 6,193,129 B1 | 2/2001 | Bittner et al. |
| 6,193,734 B1 | 2/2001 | Bolduc et al. |
| 6,206,893 B1 | 3/2001 | Klein et al. |
| 6,209,773 B1 | 4/2001 | Bolduc et al. |
| 6,245,079 B1 | 6/2001 | Nobles et al. |
| 6,248,117 B1 | 6/2001 | Blatter |
| 6,280,460 B1 | 8/2001 | Bolduc et al. |
| 6,318,616 B1 | 11/2001 | Pasqualucci et al. |
| 6,346,111 B1 | 2/2002 | Gordon et al. |
| 6,355,050 B1 | 3/2002 | Andreas et al. |
| 6,358,258 B1 | 3/2002 | Arcia et al. |
| 6,371,964 B1 * | 4/2002 | Vargas et al. ................ 606/153 |
| 6,416,527 B1 * | 7/2002 | Berg et al. .................. 606/180 |
| 6,425,900 B1 | 7/2002 | Knodel et al. |
| 6,514,263 B1 | 2/2003 | Stefanchik |
| 6,517,553 B2 | 2/2003 | Klein et al. |
| 6,520,973 B1 | 2/2003 | McGarry |
| 6,524,321 B2 | 2/2003 | Kanesaka |
| 6,530,932 B1 | 3/2003 | Swayze |
| 6,551,329 B1 | 4/2003 | Kortenbach et al. |
| 6,551,331 B2 | 4/2003 | Nobles et al. |
| 6,562,052 B2 | 5/2003 | Nobles et al. |
| 6,596,003 B1 * | 7/2003 | Realyvasquez et al. ..... 606/153 |
| 6,605,098 B2 | 8/2003 | Nobis et al. |
| 6,613,058 B1 * | 9/2003 | Goldin ....................... 606/144 |
| 6,626,917 B1 | 9/2003 | Craig |
| 6,695,859 B1 | 2/2004 | Golden et al. |
| 6,712,828 B2 | 3/2004 | Schraft et al. |
| 6,730,102 B1 | 5/2004 | Burdulis, Jr. et al. |
| 7,022,131 B1 * | 4/2006 | Derowe et al. ............. 623/1.11 |
| 7,377,927 B2 | 5/2008 | Burdulis, Jr. et al. |
| 2001/0021856 A1 | 9/2001 | Bolduc et al. |
| 2001/0023352 A1 | 9/2001 | Gordon et al. |
| 2002/0055752 A1 | 5/2002 | Schraft et al. |
| 2002/0077636 A1 | 6/2002 | Arcia et al. |
| 2002/0077637 A1 | 6/2002 | Vargas et al. |
| 2002/0082614 A1 | 6/2002 | Logan et al. |
| 2003/0176878 A1 | 9/2003 | Bolduc et al. |
| 2003/0181930 A1 | 9/2003 | Milliman et al. |
| 2004/0092965 A1 | 5/2004 | Parihar |
| 2005/0080435 A1 | 4/2005 | Smith et al. |
| 2005/0171561 A1 | 8/2005 | Songer et al. |

FOREIGN PATENT DOCUMENTS

| | | |
|---|---|---|
| EP | 0990420 | 12/2000 |
| FR | 2316910 | 7/1976 |
| WO | 98/19625 | 5/1998 |
| WO | 99/11178 | 3/1999 |
| WO | WO-99/11178 | 3/1999 |
| WO | 99/21491 | 5/1999 |
| WO | 00/12013 | 3/2000 |
| WO | 00/59380 | 10/2000 |

OTHER PUBLICATIONS

Shennib, "An Automated Interrupted Suturing Device for Coronary Artery Bypass Grafting: Automated Coronary Anastomosis", Annals of Thoracic Surgery vol. 70,(2000),1046-1048.

* cited by examiner

COMPLIANT ANASTOMOSIS SYSTEM

This patent application claims priority to U.S. Provisional Patent Application Ser. No. 60/483,079, filed on Jun. 26, 2003, which is incorporated by reference in its entirety.

FIELD OF THE INVENTION

The present invention relates generally to anastomosis, and more particularly to a system for performing a compliant anastomosis.

BACKGROUND

Anastomosis is a procedure where two separate tubular or hollow organs are surgically grafted together to form a continuous fluid channel between them. Vascular anastomosis involves creating an anastomosis between blood vessels to create or restore blood flow. When a patient suffers from coronary artery disease (CAD), an occlusion or stenosis in a coronary artery restricts blood flow to the heart muscle. In order to treat CAD, the area where the occlusion occurs is bypassed to reroute blood flow by grafting a vessel in the form of a harvested artery or vein, or a prosthesis. Anastomosis is performed between a graft vessel and two target vessels in order to bypass the blocked coronary artery, circumvent the occlusion and restore adequate blood flow to the heart muscle. This treatment is known as a coronary artery bypass graft procedure (CABG).

An anastomosis may be compliant or noncompliant. A noncompliant anastomosis is one in which the anastomosis opening in the target vessel is not substantially free to expand or contract radially. A noncompliant anastomosis may be formed with a one-piece or multiple-piece anastomosis device that compresses or otherwise controls tissue in the vicinity of the anastomosis to hold the graft vessel in place relative to the target vessel. Noncompliant anastomoses have been successful, such as when utilizing anastomosis devices deployed by Cardica's PAS-Port™ anastomosis system. A compliant anastomosis is one in which the target vessel is substantially free to expand or contract circumferentially and longitudinally in proximity to the anastomosis site. A traditional sutured anastomosis is compliant, and for this reason some surgeons would prefer to utilize an anastomosis system that provides a compliant anastomosis, particularly between a graft vessel and the aorta or other source of arterial blood.

SUMMARY

In one aspect of the invention, an integrated anastomosis tool includes an effector that both creates an opening in the wall of a target vessel and deploys a plurality of independent connectors to connect a graft vessel to the target vessel to form a compliant anastomosis. The effector includes a cutter assembly for creating the opening and a connection module for deploying the connectors. The connectors may be staples, clips or any other suitable structures or mechanisms.

In another aspect of the invention, the effector is connected to an actuator directly or indirectly. The actuator transmits energy to the effector to actuate the cutter assembly and the connection module. The actuator may store energy for transmission to the effector in any suitable form and in any suitable structure and/or mechanism. Alternately, the actuator may be connected to an external source of energy, such as compressed gas or electric power, without substantially storing energy within itself. The particular energy source used and/or the structure or mechanism for energy storage may be independent from the configuration of the effector. The actuator may be part of or connected to a handle graspable by a user.

In another aspect of the invention, the effector is connected to the actuator via an interface member. The interface member may be hinged, flexible, articulated or otherwise configured to allow the effector to be positioned at two or more different positions relative to the actuator. In this way, the effector can be oriented to facilitate the connection of the graft vessel to that target vessel, without the need to hold the actuator in an awkward position. Further, in this way the use of the effector in minimally-invasive surgery through a small incision in the patient is facilitated.

In another aspect of the invention, the cutter assembly and the connection module each may be attached to or otherwise associated with at least one transmission member such as a cable. Alternately, at least one transmission member may be a flexible shaft, a gear or gear assembly, a belt, or any other suitable mechanism. Each transmission member is in turn connected to the actuator. The cutter assembly may be actuated by motion of at least one transmission member connected to or otherwise associated with it, and the connection module may be actuated by motion of at least one transmission member connected to or otherwise associated with it. For example, a transmission member may be attached to and cause motion of a traveler, which in turn causes motion of the connection module. The transmission member or members connected to the cutter assembly may be independent from the transmission member or members connected to the connection module, to allow the cutter assembly to be actuated independently from the connection module. The cutter assembly and the connection module may be actuated sequentially by sequentially moving different transmission members.

In another aspect of the invention, the cutter assembly includes a cutter member that includes a cutter, and a holder that receives at least a portion of the cutter. The cutter may be at least partially cylindrical, and the holder may include a corresponding tubular bore therethrough. The distal end of the cutter is a cutting edge that is sharpened as by beveling, and may be circular or otherwise shaped. Further, the distal end of the cutter is tubular or otherwise substantially hollow in order to receive tissue cut from the wall of the target vessel. An auger extends from the distal end of the cutter, such as along the longitudinal axis of the tube. The auger may be threaded or fluted, or may be unthreaded and configured like a spike or spear. The auger may be fixed translationally and/or rotationally relative to the cutter. A transmission member is connected to the cutter member, and may extend through a lateral passage in the holder. Motion of at least one transmission member associated with the cutter assembly may both rotate and advance the cutter. As one example, a portion of the outer surface of the cutter member is threaded, and the transmission member is a cable wound along the threads, such that motion of the cable rotates and advances the cutter.

In another aspect of the invention, the effector includes at least one registration element that is configured to maintain the effector in substantially the same location relative to the target vessel throughout actuation of the effector. As one example, a number of registration elements extend distally from the effector and are configured to engage the tissue of the target vessel. Optionally, at least one registration element is configured to test the thickness and/or tissue quality of the wall of the target vessel. Each registration element has a cross-section area small enough that its separation from the target vessel causes at most minimal leakage through the wall of the target vessel. Optionally, one or more thickness sensors may be provided independent from the registration element or elements.

In another aspect of the invention, a graft vessel is loaded onto the connection module. The connection module is moved to the closed position if it is not already in the closed position, and a graft vessel is pulled through a passage in the connection module such as by a pull-through tool or tools. Advantageously, the connection module allows side loading and release of the graft vessel to provide greater surgical flexibility. An end of the graft vessel is everted over at least a part of each connector.

In another aspect of the invention, after the graft vessel has been loaded onto the connection module, the connection module is loaded into the effector if it is not already in the effector. The distal end of the effector may be placed on the target vessel at a potential anastomosis site. The effector may include a port or other opening therein to allow the operator to better visualize the intended anastomosis site. At least one registration element engages the target vessel as the effector is placed against it.

In another aspect of the invention, optionally at least one registration element is configured to measure the thickness of the wall of the target vessel. Where the wall of the target vessel is the proper thickness for anastomosis, fluid enters the hollow interior of the registration element through its distal end and exits through the aperture, providing visual confirmation that the tissue of the wall of the target vessel is of suitable thickness and is not calcified. Where the wall of the target vessel is too thick, or is calcified, no fluid exits the aperture because the end of the registration element has not penetrated the wall of the target vessel completely, and the potential anastomosis site is not suitable. The operator then removes the effector from the target vessel and places it at a different potential anastomosis site on the target vessel. In this way, an operator can easily determine whether the selected anastomosis site on the target vessel is appropriate.

In another aspect of the invention, after the effector is registered to the target vessel, the cutter assembly is actuated by the corresponding transmission member to create an opening in the wall of the target vessel. Where the transmission member is a cable wound about at least a portion of the cutter member, the proximal motion of the cable causes the cutter to advance as well as rotate about its longitudinal axis. The bore in the holder guides and stabilizes the cutter as it advances. As the cutter advances and spins, it enters the tissue of the target vessel through the aperture in the stop at the distal end of the effector, and creates an opening therein. The auger may be fixed longitudinally relative to the cutter, such that it advances longitudinally at the same rate as the cutter.

In another aspect of the invention, after the cutter creates an opening in the wall of the target vessel, it is moved out of the way of the connection module. For example, where the transmission member attached to the cutter is a cable, it becomes taut when no more cable remains to pull through the passage in the holder, and then exerts a proximal tensile force on the cutter assembly. In response to that proximal force, the cutter assembly moves proximally, out of and then away from the opening in the target vessel. The cutter assembly then moves in a direction that has a component substantially perpendicular to the direction of its previous longitudinal motion. Alternately, the cutter assembly moves in a different direction relative to the direction of its previous longitudinal motion, such as by rotating on an axis away from that direction. The cutter assembly and the connection module initially may be arranged substantially along an axis, where the cutter assembly is movable away from that axis before the connection module is shuttled distally. In this way, the cutter assembly is moved out of the way of the connection module.

In another aspect of the invention, the connection module is actuated by a corresponding transmission member, and translates distally toward the opening. Distal motion of the connection module may cease when it contacts a stop. At that time, where the connectors are staples, a tine of each staple may extend through the opening in the wall of the target vessel created by the cutter assembly, and another tine of each staple may penetrate completely through the wall of the target vessel. The connection module may include at least one plate that has a number of apertures defined in it and an anvil extending into each aperture. A staple is positioned adjacent to each anvil, and may be held in place by that anvil. Each plate may rotate, such as about the longitudinal centerline of the connection member. One or more drivers are located proximal to the staples, and are movable distally to push each staple distally against the corresponding anvil.

In another aspect of the invention, the connection module quickly shuttles distally and deploys the connectors after the cutter assembly has been moved out of the way. Advantageously, the connection module shuttles distally and deploys the connectors in one second or less. Because of the short duration between creation of the opening in the wall of the target vessel and completion of the anastomosis, hemostasis need not be maintained, as only a small amount of fluid escapes through the opening in the target vessel. In this way, construction of the effector is simplified.

In another aspect of the invention, after the connection module substantially stops its distal motion, force is still exerted on the connection module in the distal direction. This force pushes on the driver or drivers, which in turn exert a force on the connectors in a distal direction that deploys them, anastomosing the graft vessel to the target vessel. The motion of the driver or drivers exerts a force against each connector, which deforms upon contact with the corresponding anvil. Alternately, the connectors are self-deforming, and the force exerted by the driver or drivers is applied to the connection module in a manner that releases the connectors for self-deformation. After the connectors have been deployed, the anastomosis is complete. Each plate is rotated or otherwise moved to clear the anvils out of the way and release the connectors from the connection module through the apertures in the plate.

In another aspect of the invention, where staples are used as connectors, one tine of each staple may extend through and bends substantially radially outward from the opening in the wall of the target vessel, thereby contacting the inner surface of the wall of the target vessel without penetrating it in response to the force exerted by the driver or drivers. That tine penetrates the wall of the graft vessel, either as part of the prior preparation of the graft, or in response to the force exerted by the driver or drivers. Further, in response to that force another tine of each staple may penetrate, partially or completely, the wall of the target vessel from the outside. Optionally, that tine may penetrate the wall of the graft vessel.

In another aspect of the invention, after the connectors have been deployed, the connection module moves to the open position, releasing the graft vessel. For example, the connection module may be biased to the open position, and distal force exerted against the connection module may release a catch that previously had overcome that bias to hold the connection module closed. The effector is then removed from the target vessel.

BRIEF DESCRIPTION OF THE DRAWINGS

The use of the same reference symbols in different figures indicates similar or identical items.

DETAILED DESCRIPTION

This specification describes an exemplary embodiment of an integrated anastomosis tool and an exemplary method for using that tool.

Integrated Anastomosis Tool

Figure 1:
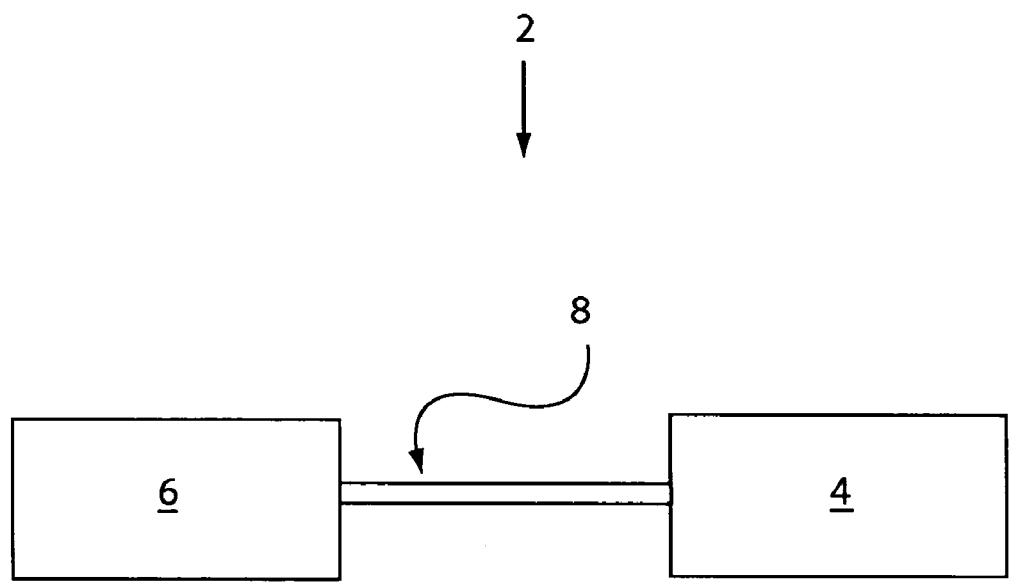
FIG. 1 is a schematic view of an integrated anastomosis tool having an actuator and an effector.

Referring to FIG. 1, an integrated anastomosis tool 2 includes an effector 4 connected to an actuator 6, such as by an interface member 8. The interface member 8 may be flexible, articulated, hinged or otherwise configured in any suitable manner to allow the effector 4 to be positioned at two or more different positions relative to the actuator 6. That is, the interface member 8 may be bent, manipulated or otherwise moved such that the effector 4 may be positioned in more than one orientation relative to the actuator 6. Articulation or other motion of the interface member 8 may be located anywhere along the length of the interface member 8, or on the effector 4 or actuator 6. Alternately, control of the articulation may be integrated into the actuation sequence of the tool 2. In this way, the effector 4 can be oriented by the user to facilitate the connection of a graft vessel to a target vessel without the need to hold the actuator 6 in an awkward position. Alternately, the interface member 8 may be rigid. Alternately, the effector 4 may be connected directly to the actuator 6. For example, the effector 4 and actuator 6 may be fixed mechanically relative to one another, such as by securing both the effector 4 and actuator 6 to a common frame or housing.

Actuator

The actuator 6 may be connected operationally to the effector 4 by one or more transmission members (not shown). At least one transmission member may be a cable, a rod, a belt, a chain, a tube or other structure for transmitting fluid or hydraulic pressure, one or more electrical wires and/or motors, or any other suitable structure or mechanism. Where more than one transmission member is utilized, one or more of the transmission members may be configured differently from one or more of the others. For example, the transmission members may include a cable used in conjunction with a rod. The actuator 6 is operationally connected to the effector 4 by one or more transmission members, and as a result the mechanical configuration of the actuator 6 is independent of the mechanical configuration of the effector 4. That is, because the actuator 6 interfaces with the effector 4 via the transmission member or members, the actuator 6 may be any mechanism capable of actuating the transmission members in such a way as to operate the effector 4. In this way, the effector 4 presents a standard interface to the actuator 6, such that any actuator 6 that meets the standard interface may be utilized. The design of a particular configuration of the actuator 6 to achieve desired motion of one or more transmission members is within the capability of one skilled in the art. Alternately, the actuator 6 is directly connected to the effector 4, and transmission members are not used, such that the mechanical configurations of the actuator 6 and of the effector 4 are not independent.

The actuator 6 transmits energy to the effector 4 to actuate it, such as via the one or more transmission members. The actuator 6 may store energy for transmission to the effector 4. Such energy may be stored in any suitable form, and in any suitable structure and/or mechanism. As one example, a reservoir of compressed gas such as carbon dioxide, argon or nitrogen is included within or connected to the actuator 6, in which energy is stored in the form of gas pressure. As another example, a battery or batteries are included within or connected to the actuator 6, such that electrical energy is stored. As another example, a spring or springs are included within or connected to the actuator 6 and deformed, such that energy is stored as a result of the deformation of that spring or springs. Other types of energy may be stored by different or additional mechanisms within or connected to the actuator 6, if desired. Alternately, the actuator 6 may be connectable to an external source of energy used to transmit force to the effector 4, instead of or in conjunction with an internal energy source within the actuator 6. As one example, the actuator 6 may be connectable to an external electrical outlet that provides AC or DC power. As another example, the actuator 6 may be connectable to an external source of compressed gas, such as carbon dioxide or nitrogen. As another example, the actuator 6 may be connectable to an external vacuum source. Such vacuum may be utilized, for example, to draw ambient air into and/or through the actuator 6 to drive an impeller, thereby generating energy for transmission to the effector 4. Other types of energy may be received from an external source by the actuator 6. The particular energy source utilized and/or the structure or mechanism for energy storage is independent from the configuration of the effector 4. Alternately, energy is stored in the effector 4, or received from a source other than the actuator 6 by the effector 4, and the actuator 6 controls the application of such energy without substantially storing or transmitting it.

The actuator 6 may form, be part of or be connected to a handle (not shown) of the integrated anastomosis tool 2 that is graspable by a user. Alternately, or additionally, the effector 4 may form, be part of or be connected to a handle (not shown) of the integrated anastomosis tool 2 that is graspable by a user. The use of two handles may be advantageous where the interface member or members 8 are substantially flexible. At least one handle may be configured to facilitate its handling by a robotic end effector or other mechanism.

Effector

Figure 2:
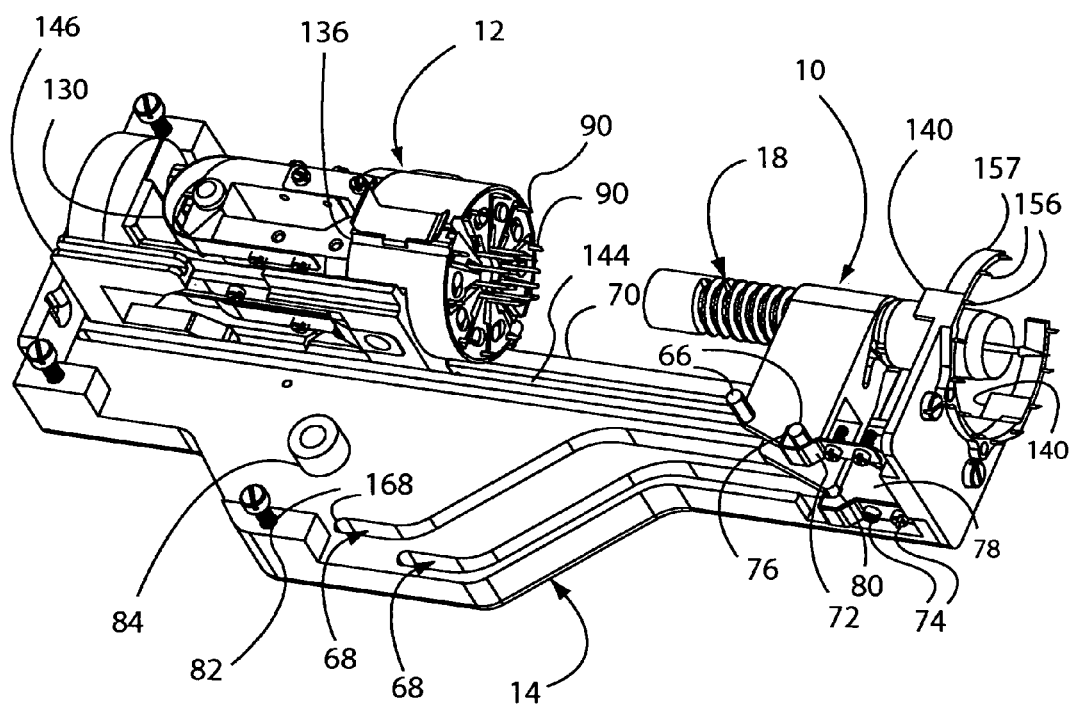
FIG. 2 is a perspective view of an exemplary effector.

Referring also to FIG. 2, the effector 4 includes a frame 14, and a cutter assembly 10 and a connection module 12 that are both movable relative to the frame 14. Alternately, at least one of the cutter assembly 10 and the cutter deployment array 12 is substantially fixed relative to at least part of the frame 14, where that part of the frame 14 may or may not be movable relative to a remainder of the frame 14. The cutter assembly 10 creates an opening in the wall of a target vessel, and the connection module 12 connects a graft vessel to the target vessel, such as by deploying one or more connectors 90.

Cutter Assembly

Figure 3:
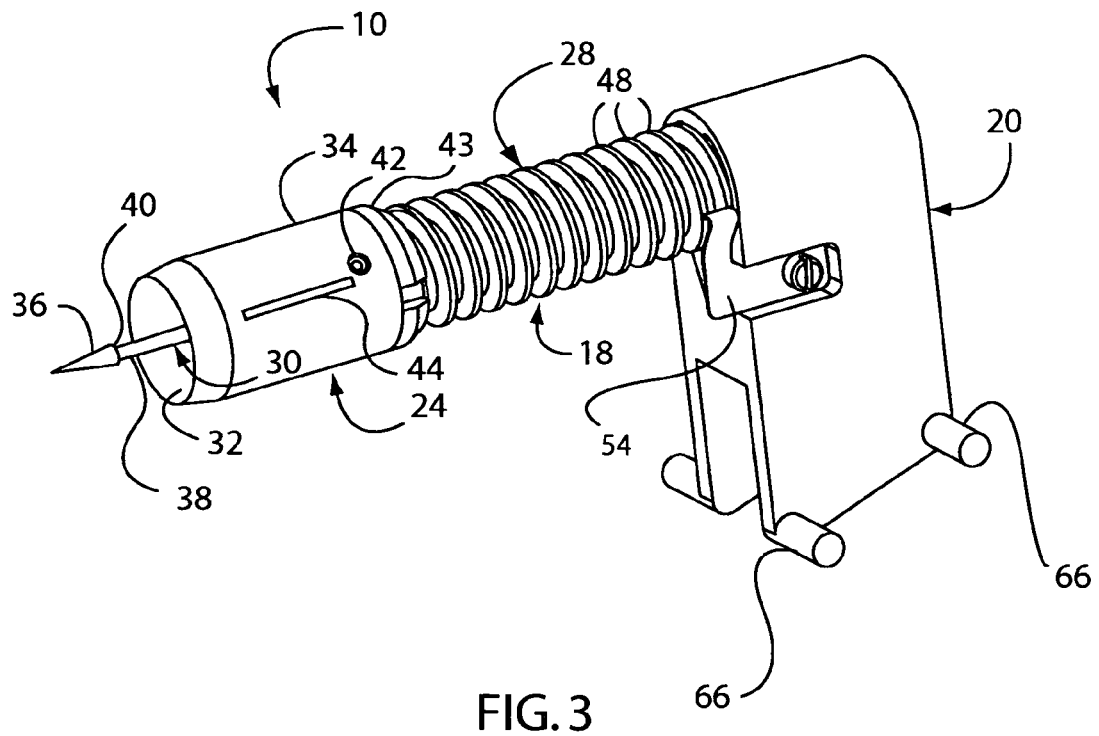
FIG. 3 is a perspective view of an exemplary cutter assembly of an effector.
Figure 4:
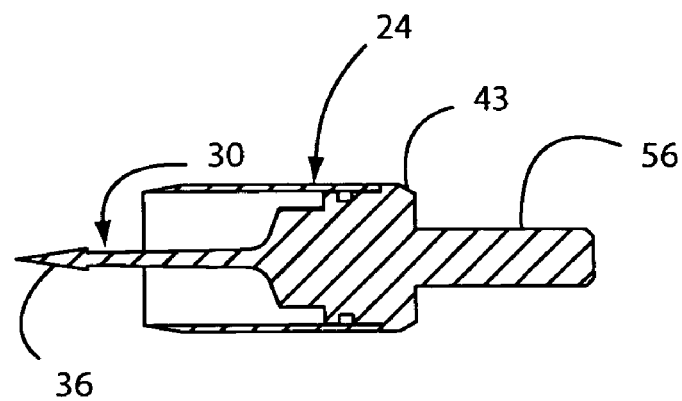
FIG. 4 is a cross-section view of a cutter member of the cutter assembly.

Referring also to FIGS. 3-4, the effector 4 includes a cutter assembly 10. The cutter assembly 10 includes a cutter member 18, and a holder 20 with a bore 22 defined therein that receives at least a portion of the cutter member 18. The bore 22 may extend partly into or completely through the holder 20. The cutter member 18 includes a cutter transport 28 connected to a cutter 24, where the cutter 20 is distal to the cutter transport 28. The cutter 24 may be fixed to an auger 30, either of which may be configured as described in U.S. patent application Ser. No. 10/054,745 or U.S. patent application Ser. No. 10/659,057, both of which are incorporated by reference herein in their entirety.

The cutter 24 is constructed from a metal, such as stainless steel, but a different material may be used if desired. The cutter 24 may be constructed from biocompatible material, if desired. As one example, the cutter 24 is a hollow tubular structure with an open distal end. The distal end of the cutter 24 has a substantially circular shape, and the cutter 24 has a substantially circular cross-section along its length. However, at least part of the cutter 24 may take another shape, have a different cross section, or vary in cross sectional perimeter or area along its length. For example, the cutter 24 may take the shape of a tube having an open slit along its length. That is, the cutter 24 may form the majority of a cylindrical surface, where the cutter 24 extends along, for example, 350° of the complete 360° perimeter of the cylinder. Alternately, the distal end of the cutter 24 may be angled relative to its longitudinal axis, if desired. That is, the distal end of the cutter 24 may be coincident with a plane angled relative to the longitudinal axis of the cutter 24.

The proximal end of the cutter 24 has a larger diameter than the cutter transport 28, such that a shoulder 43 results from that difference in diameter. The shoulder 43 may be circumferential. Alternately, the shoulder 43 may include one or more separate segments. Alternately, the cutter 24 has the same diameter or a smaller diameter than the cutter transport 28, and the shoulder 43 is at least one stub or other structure that extends outward further than the outer surface of the cutter transport 28 adjacent to the cutter 24.

The distal end of the cutter 24 is sharpened to cut the wall of a tubular vessel, such as the aorta or other blood vessel. For example, the distal end of the cutter 24 may be beveled for sharpness. The distal end of the cutter 24 may be beveled inward, such that an inner surface 32 of the cutter 24 contacts a vessel wall before an outer surface 34 of the cutter 24, or beveled outward, such that the inner surface 32 contacts a vessel wall after the outer surface 34. Alternately, the distal end of the cutter 24 may be beveled both inward and outward, such that a sharp edge is provided at a location between the inner surface 32 and outer surface 34 of the cutter 24. Alternately, less than the entire circumference of the distal end of the cutter 24 is sharpened. Alternately, the distal end of the cutter 24 is at least partially serrated.

The inner surface 32 may be substantially smooth. Alternately, at least a portion of the inner surface 32 may be rough to facilitate capture of tissue removed from the wall of a target vessel by increasing the coefficient of friction between the inner surface 32 and captured tissue. Alternately, the inner surface 32 may include one or more tissue plug capture features (not shown) defined therein to facilitate capture of tissue removed from the wall of a target vessel. The outer surface 34 of the cutter 24 may be substantially smooth as well.

The cutter 24 is connected to an auger 30, which may be constructed from the same biocompatible metal as the cutter 24 or from a different biocompatible material. The auger 30 may be substantially coaxial with the cutter 24. The auger 30 may be connected to the cutter 24 indirectly via the cutter transport 28. That is, the auger 30 may be connected to or formed integrally with the cutter transport 28, which in turn is connected to the cutter 24. The auger 30 is fixed relative to the cutter 24, such that the auger 30 and cutter 24 both translate and rotate together at the same rates. Alternately, the auger 30 is translationally fixed relative to the cutter 24 such that the auger 30 and cutter 24 translate at the same rate, but is at least partially free to rotate relative to the cutter 24. For example, the auger 30 may include a circumferential flange (not shown) held within a corresponding groove (not shown) in the cutter 24. The flange can rotate within the groove, and contact between the flange and the groove causes the auger 30 and cutter 24 to translate together. In such an embodiment, the auger 30 and the cutter 24 are fixed axially, but independent rotationally. Other mechanisms or structures may be used to allow the auger 30 and the cutter 24 to translate together axially while having the capability of rotating at least partially independently.

The auger 30 includes a spike 36 at its distal end, and a shaft 38 extending proximally from the spike 36. The distal end of the spike 36 extends distally to the distal end of the cutter 24. The shaft 38 is substantially cylindrical. Alternately, the shaft 38 may be shaped differently. The distal end of the spike 36 is sharp to allow it to readily penetrate tissue. For example, the spike 36 may be tapered from its proximal end toward its distal end, and may be substantially axisymmetric. The proximal end of the spike 36 may be wider than the shaft 38, such that a ledge 40 is formed at the proximal end of the spike 36. Further, the spike 36 may be positioned relative to the cutter 24 and is shaped such that the ledge 40 is distal to the distal end of the cutter 24. Alternately, the ledge 40 is positioned proximal to the distal end of the cutter 24.

The auger 30 may be configured differently, if desired. As one example, the auger 30 may be threaded, with a sharp distal end to facilitate its entry into the wall of a target vessel. Such an auger 30 may be tapered as well. Alternately, the auger 30 may be a needle that is solid or at least partially hollow. As an example, the needle may be simply a length of hypotube. As another example, the needle is a thin solid rod. The needle may be pointed or sharpened at its distal end. However, the needle may have a diameter small enough that its distal end is sharp enough to readily penetrated tissue as a consequence of its size. Alternately, the auger 30 is a barb, harpoon, lance, corkscrew or other suitable symmetrical or non-symmetrical structure. Alternately, more than one auger 30 is utilized, or the auger 30 includes a number of individual components. For example, a number of augers 30 may be clustered together in proximity to the longitudinal axis of the cutter 24. Alternately, the auger 30 may be omitted altogether.

The cutter 24 may be attached to the cutter transport 28 and/or the auger 30 by dimpling the cutter 24 against the cutter transport 28 in one or more locations. The cutter transport 28 may have a groove (not shown) defined at least partially circumferentially around it. Each dimple 42 is formed by pressing the cutter 24 inward toward the groove, causing that location on the cutter 24 to deform into a dimple 42. The dimple 42 expands into a portion of the groove, trapping at least part of the dimple 42 therein. The cutter 24 thus is fixed relative to the auger 30, such that they rotate and translate together. The auger 30 may be connected to the cutter 24 using any other or additional suitable mechanism, structure or method. For example, the auger 30 and the cutter 24 may be molded or otherwise formed together as a single piece. As another example, the auger 30 and the cutter 24 may be fixed together by adhesive. As another example, the auger 30 and the cutter 24 may be fixed together by welding, or may be pinned or screwed together.

Figure 5:
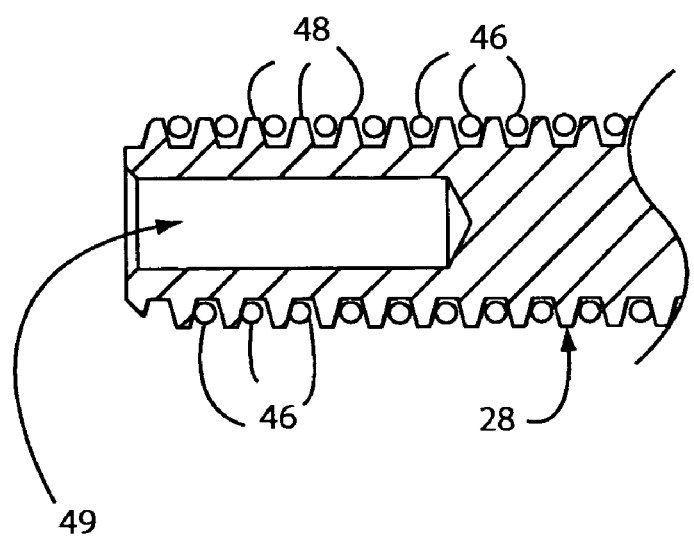
FIG. 5 is a cross-section view of the cutter member showing a cutter cable wrapped around a portion thereof.

Referring also to FIGS. 4-5, a centerpiece 56 may extend distally from the cutter transport 28. The centerpiece 56 may be formed into the cutter transport 28 as an integral component thereof, or may be a separate piece that is connected to the cutter transport 28 in any suitable manner, such as by welding, soldering, or adhesive. The cutter 24 may be connected to the centerpiece 56, and may be connected to the cutter transport 28 indirectly via the centerpiece 56.

At least one cutter vent 44 may be defined in the cutter 24, providing a pathway for fluid such as air or blood to escape from the cutter 24 when the cutter 24 and auger 30 are deployed into the target vessel. Thus, the cutter vent or vents 44 prevent fluid from becoming trapped within the cutter 24, because the pressure of that trapped fluid otherwise could potentially prevent the cutter 24 from penetrating the vessel wall or other anatomical structure. The cutter vent or vents 44 are defined in the cutter 24 at or proximal to the proximal end of the cutter 24. Alternately, the cutter vent or vents 44 are located at the proximal end of the cutter 24, at its connection to the cutter transport 28. Each cutter vent 44 may be shaped in any appropriate manner. For example, a cutter vent 44 in the cutter 24 may be substantially straight, extending longitudinally, transversely or diagonally, or may be curved and extend at least partially in the longitudinal direction; for example, it may be helical or sinusoidal.

The cutter transport 28 may be any structure or mechanism suitable for advancing the cutter 24. As one example, the cutter transport 28 is a rod or other member that is at least partially threaded with a number of threads 48. The crests of the threads 48 may be flat, rounded, angled or shaped in any other appropriate manner. Referring also to FIG. 5, a transmission member such as a cutter cable 46 is wound along at least some of the threads 48 of the cutter transport 28. The difference between the major diameter and the minor diameter of the threaded area of the cutter transport 28 may be at least twice the diameter of the cutter cable 46. In this way, the cutter cable 46 is held within the threads 48 and does not extend outward further than the crests of the threads 48. Alternately, the cutter cable 46 does extend outward further than the crests of the threads 48; for example, where the cutter cable 46 is wound around threads 48 of the cutter transport 28 proximal to the holder 20. An end of the cutter cable 46 may be fixed to the cutter transport 28 in any suitable manner. The anchor feature 50 may be located proximal to the threaded area of the cutter transport 28. As one example, the anchor feature 50 is a hole or passage extending into or through the cutter transport 28. An end of the cutter cable 46 is inserted into that anchor feature 50, then welded, fastened, clipped, tied or otherwise fixed to the anchor feature 50. As another example, the anchor feature 50 is a slot at the proximal end of the cutter transport 28 to which an end of the cutter 46 is connected. Alternately, the anchor feature 50 receives the cutter cable 46 and allows the end of the cutter cable 46 to move relative to the cutter transport 28. Alternately, the anchor feature 50 is located in or distal to the threaded area of the cutter transport 28. Any suitable structure, mechanism or method may be used to connect the cutter cable 46 to the cutter transport 28 either directly or indirectly. The cutter transport 28 may include a bore 49 or other feature to receive the centerpiece 56 of the cutter 24.

The cutter transport 28 is received in the bore 22 of the holder 20. The bore 22 may be created in the holder 20 in any suitable manner, such as by molding it into the holder 20 or machining it through the holder 20. The bore 22 may be substantially smooth-walled, with a diameter slightly greater than the major diameter of the threaded area of the cutter transport 28. The fit between the major diameter of the threaded area of the cutter transport 28 and the bore 22 is selected to permit the cutter transport 28 to rotate smoothly within the bore 22 substantially without binding. The diameter of the bore 22 and its length are also selected to reduce or eliminate precession of the cutter transport 28 and cutter 24 during operation of the cutter assembly 10. Alternately, the bore 22 is threaded. Where the cutter cable 46 does not enter the bore 22, the threads of the bore 22 and the threads 48 of the cutter transport 28 may be closely matched to one another. Alternately, if the cutter cable 46 enters the bore 22, the crests of the threads of the bore 22, and the depth of the roots of the threads 48 of the cutter transport 28, are sized such that adequate space exists between them to accommodate the cutter cable 46 on the cutter transport 28.

Figure 3A:
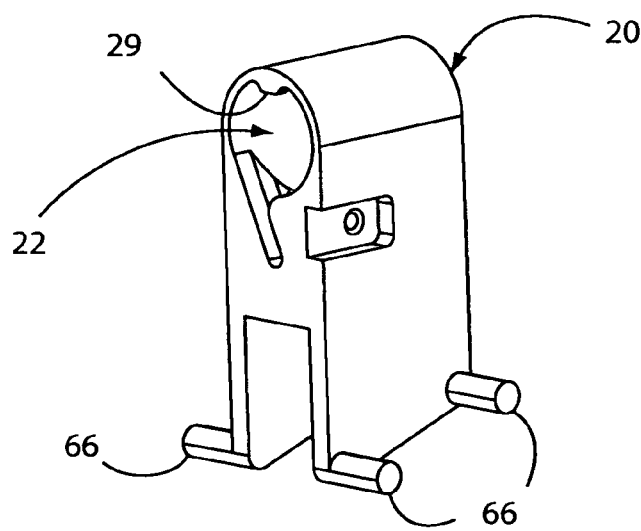
FIG. 3A is a perspective view of an exemplary holder that may be used in the cutter assembly.

Referring also to FIG. 3A, a tooth 29 may be located in or at the edge of the bore 22. The tooth 29 is sized to engage the threads 48 of the cutter transport 28 to provide stability to the cutter transport 28 and substantially prevent axial slide of the cutter transport 28 during its actuation, without substantially impeding motion of the cutter transport 28.

The cutter cable 46 is wound around at least a portion of the cutter transport 28 proximal to the holder 20, and remains proximal to the holder 20 and outside of the bore 22 during actuation. Optionally, a cable passage (not shown) extends outward from the bore 22 of the holder 20 to an outer surface of the holder 20. Where the cable passage is used, the cutter cable 46 is wound around at least a portion of the cutter transport 28 that is positioned within the bore 22. The cable passage is sized and shaped to receive the cutter cable 46 therethrough. The cable passage has a surface finish along its interior and at each end such that the cutter cable 46 can move smoothly through it when the cutter assembly 10 is actuated, as described in greater detail below. The cable passage is substantially straight, and may be oriented substantially tangent to the surface of the cutter transport 28, or in a different direction relative to the cutter transport 28. Further, the cable passage may be oriented such that its axis, extended outward, intersects the cutter transport 28 at a location between its major diameter and its minor diameter, to facilitate the smooth unwinding of the cutter cable 46 from the cutter transport 28. Alternately, the cable passage is curved, at least in part. Alternately, the cable passage is oriented differently.

The holder 20 may include at least one projection 66 extending therefrom. Advantageously, two or more projections 66 extend laterally from each side of the holder 20 to provide added stability. The projection or projections 66 may be flanges, pins or any other suitable structures that are integral with or that are attached to the holder 20. The projection or projections 66 may extend substantially perpendicular to the longitudinal axis of the cutter member 18. Alternately, the projection or projections 66 may extend at a different angle relative to the longitudinal centerline of the cutter member 18. The projection or projections 66 may extend from the base of the holder 20 or from any other portion of the holder 20.

Alternately, instead of a cutter 24 and auger 30, a knife (not shown) or other structure or mechanism can be provided. The knife or other mechanism may be configured to create a linear, rather than curved, opening in the target vessel. For example, the knife may be movable in a direction substantially parallel to the longitudinal centerline of the target vessel in order to create a substantially linear incision therein. Where the knife or other mechanism is configured to create a linear incision, the cutter transport 28 may be configured to move the knife or other mechanism in a linear rather than rotational manner.

Frame

Referring also to FIG. 2, the frame 14 includes one or more first grooves 68 defined therein. The frame 14 may be formed of any suitable material, such as polycarbonate or stainless steel, and the groove or first grooves 68 may be formed in any suitable manner, such as by molding or machining. Each first groove 68 is configured to receive at least one projection 66 and guide the motion thereof. The groove or first grooves 68 form a path along which the projections 66, and thus the holder 20 and the cutter assembly 10, can travel, and that path may extend in any direction or combination of directions that allows for motion of the cutter assembly 10 in a desired manner. As one example, at least one first groove 68 is defined in each side wall 70 of the frame, and the first grooves 68 guide the cutter assembly 10 proximally relative to its original position and away from the line defined by the original position of the longitudinal axis of the cutter member 18. Motion away from the line defined by the original position of the longitudinal axis of the cutter member 18 may be referred to as off-axis motion. In this way, the cutter assembly 10 is movable out of the way of the connection module 12 after the cutter assembly 10 creates an opening in the wall of the target vessel. The interaction between each projection 66 and the corresponding first groove 68 may also act to minimize or prevent motion of the cutter assembly 10 in the lateral or vertical directions. Alternately, the frame 14 has one or more rails, projections or ribs extending therefrom, and the holder 20 includes one or more grooves corresponding to those projections. Alternately, any other or additional appropriate structure or mechanism may be used to guide the motion of the cutter assembly 10 relative to the frame 14. As one example, the cutter assembly 10 is rotatable out of the way of the connection module 12 after the cutter assembly 10 creates an opening in the wall of the target vessel. The cutter assembly 10 is retracted proximally to a suitable location, then moved off-axis by rotation. Such rotation may result from a passive mechanism such as a spring, an active mechanism such as a device that engages the cutter cable 46 or other cable, or a combination of active and passive mechanisms. Where such a system is utilized, the first grooves 68 optionally may be omitted.

One or more clips 72 may be connected to the frame 14, such as by screws 74. Alternately, the clip or clips 72 may be formed into the frame 14 or otherwise connected to the frame 14. Each clip 72 is shaped and positioned to hold at least one projection 66 of the holder 20, and substantially to restrain that projection 66 against longitudinal motion in the proximal and/or distal direction, both before actuation of the cutter assembly 10 and while the cutter assembly 10 creates an opening in the wall of the target vessel. Each clip 72 may be shaped in the same manner as or in a different manner from any other clip 72. As one example, each clip 72 is a leaf spring extending proximally from its connection to the frame 14, with an upwardly-extending stop 76 formed into its proximal end. The stop 76 is located proximal to the corresponding projection 66, and substantially restrains the corresponding projection 66 and thereby the holder 20 and the cutter assembly 10 against proximal motion. The clip or clips 72 are constructed such that the clip or clips 72, taken together, resist an amount of force in the proximal direction that is greater than the amount exerted on the cutter assembly 10 during forward travel of the cutter member 18 and less than the amount exerted on the cutter assembly 10 by the cutter cable 46 after the forward travel of the cutter member 18 is complete. In this way, the clip or clips 72 allow motion of the cutter cable 46 to move the cutter member 18 distally, rather than move the cutter assembly 10 as a whole proximally, and thereby allow the cutter assembly 10 to create an opening in the target vessel. Actuation of the cutter assembly 10 and the forces acting upon the cutter assembly 10 are described in greater detail below.

At least one bracket 78 may be connected to the frame 14 in any suitable manner, or formed into the frame 14. Each bracket 78 is positioned in proximity to a corresponding clip 72. Alternately, at least one bracket 78 is not associated with a clip 72, or is spaced apart from a corresponding clip 72. Each bracket 78 includes an indentation 80 defined therein, where that indentation 80 is located distal to the stop 76 of the corresponding clip 72. The indentation 80 may be positioned relative to the corresponding stop 76 such that the distance between the distal surface of the stop 76 and the most-distal portion of the indentation 80 is substantially equal to or slightly greater than the length of the projection 66 held therebetween. In this way, the projection 66 is held securely. Contact between each bracket 78 and one or more corresponding projections 66 substantially restrains distal motion of the holder 20 during actuation of the cutter assembly 10. In combination with the corresponding stop or stops 76, the bracket or brackets 78 restrain the holder 20 substantially in place in the longitudinal direction during actuation of the cutter assembly 10. Further, contact between the projection or projections 66 and the corresponding groove or first grooves 68 restrains the holder 20 substantially in place in the lateral and vertical directions. For convenience, the term "vertical" refers to the direction that is substantially perpendicular to both the longitudinal direction and to the lateral direction, and is independent of the orientation of the integrated anastomosis tool 2 relative to a patient or to an operating room. In addition, contact between the sides of the holder 20 and the inner surface 82 of each side wall 70 of the frame 14 also may restrain the holder 20 substantially in place in the lateral direction. Thus, the holder 20 is substantially restrained in all three dimensions as the cutter member 18 is actuated to create an opening in the target vessel. Such restraint allows the cutter assembly 10 to produce an opening of the desired quality in and in a desired location on the target vessel. Alternately, the holder 20 may be free to move at least partially in at least one direction during actuation of the cutter assembly 10.

As used in this document, the term "impulse" means a force that acts on a body for a short time but produces a large change in its linear or angular momentum. The cutter assembly 10 is configured to be actuated impulsively. That is, an impulse is applied to the cutter assembly 10 to cause it to make an opening in the target vessel and to move off-axis out of the way of the connection module 12. Alternately, the cutter assembly 10 is configured to be actuated non-impulsively. Further detail regarding the impulsive actuation of the cutter assembly 10 is provided below.

Connection Module

The effector 4 includes a connection module 12, which may be any mechanism that is configured to connect a graft vessel to a target vessel. As one example, the connection module 12 may deploy one or more staples, clips, connectors or other mechanisms to connect the graft vessel to the target vessel. As another example, the connection module 12 may be configured to suture the graft vessel to the target vessel, such as by moving one or more needles that are connected to suture in order to suture the vessels together. As another example, the connection module 12 may be configured to adhere the graft vessel to the target vessel, such as by placing adhesive such as fibrin glue therebetween. As another example, the connection module 12 may be configured to apply RF energy to the graft vessel and/or the target vessel to connect the two together. The connection module 12 may be configured in any other suitable manner for connecting the graft vessel to the target vessel.

Figure 6:
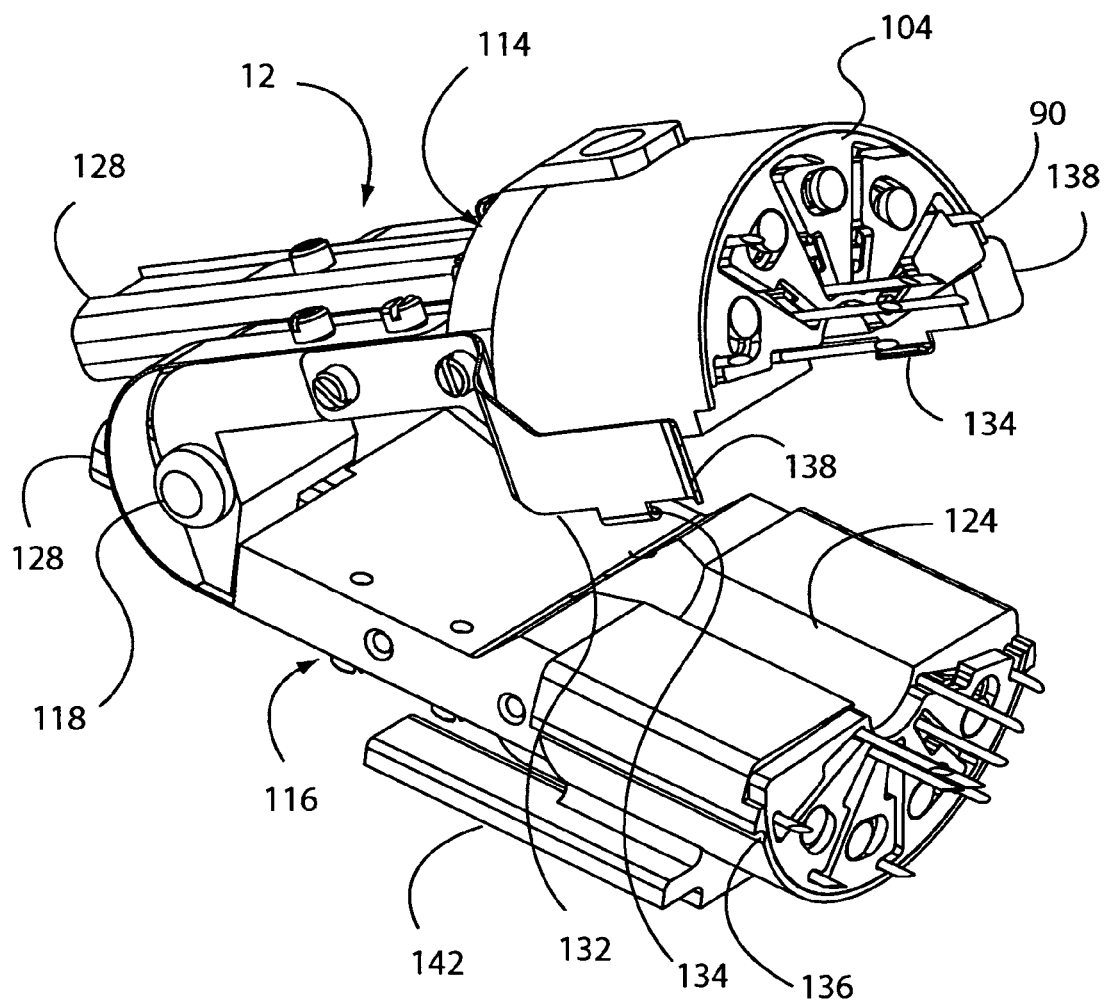
FIG. 6 is a perspective view of one example of a connection module of an effector of an integrated anastomosis tool, where the connection module is in an open position.
Figure 7:
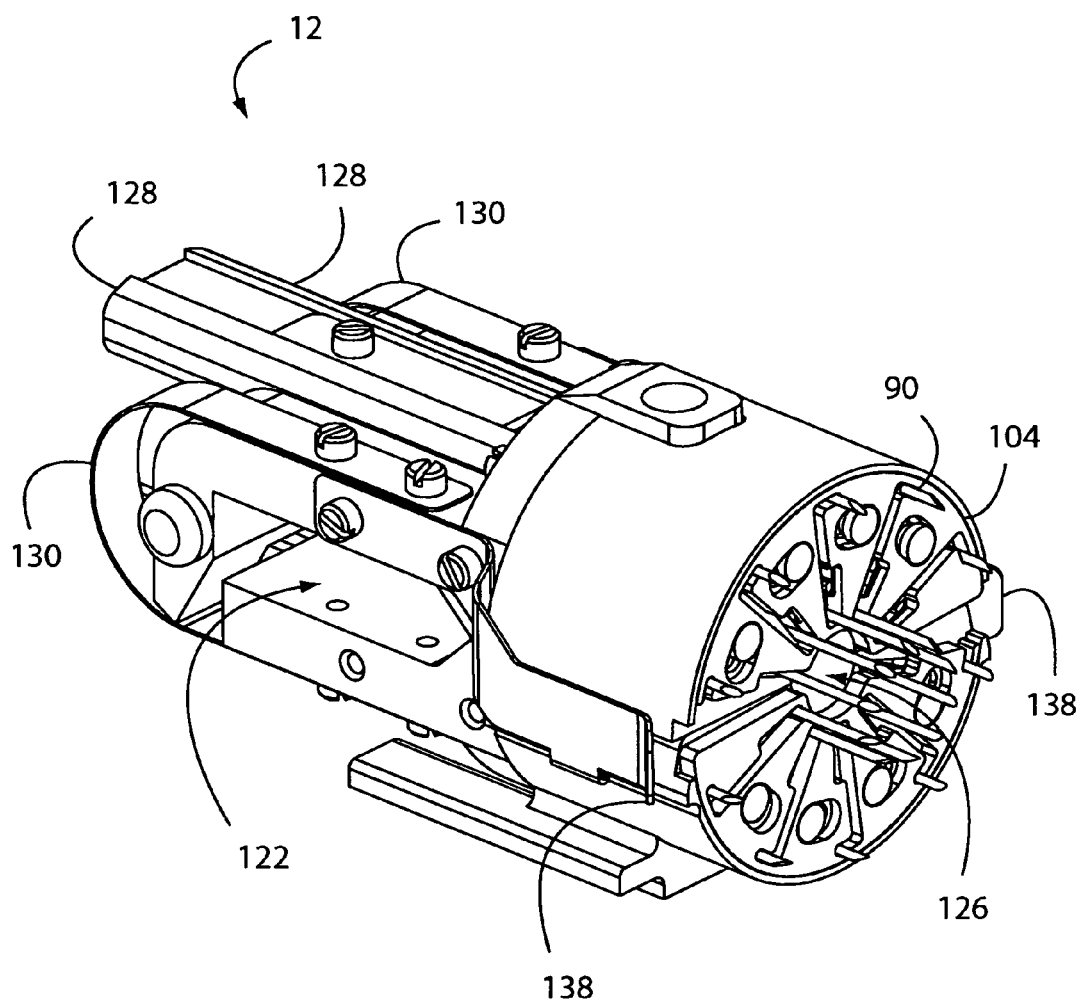
FIG. 7 is a perspective view of the connection module of FIG. 6 in a closed position.
Figure 8:
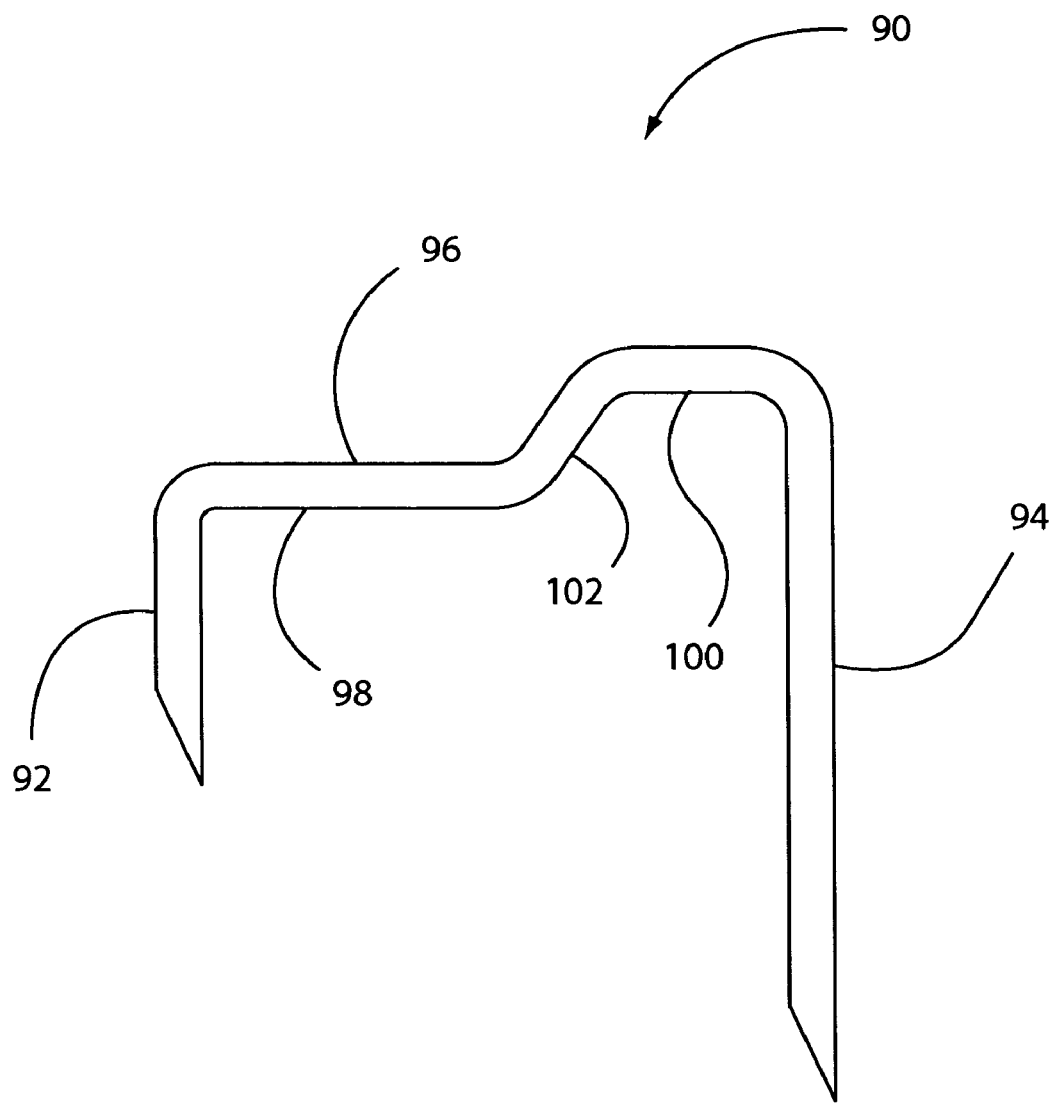
FIG. 8 is a front view of an exemplary connector that may be used in conjunction with the connection module.

Referring to FIG. 2 and to FIGS. 6-7, an exemplary connection module 12 connects an end of a graft vessel to the side of a target vessel by deploying a plurality of connectors 90. The connectors 90 may be substantially the same as one another, or one or more connectors 90 may be configured differently than one or more of the others. The connectors 90 may be staples, clips or other structures or mechanisms configured to connect tissue of the graft vessel to tissue of the target vessel. In one embodiment, at least one of the connectors 90 is a staple 90. Referring to FIG. 8, an exemplary staple 90 includes a first tine 92 and a second tine 94, each connected to a base 96. The proximal end of each tine 92, 94 is connected to the base 96. Alternately, a different part of the first tine 92 and/or the second tine 94 is connected to the base. The tines 92, 94 are substantially parallel to one another. Alternately, the tines 92, 94 are oriented differently relative to one another. The first tine 92 is shorter than the second tine 94. Alternately, the first tine 92 is the same length as or longer than the second tine 94. Each tine 92, 94 may have a sharp point at its distal end. Alternately, at least one of the tines 92, 94 may not be sharp at its distal end, instead relying on its diameter being small enough to pierce tissue. The base 96 of the staple 90 may be stepped, where a first step 98 is substantially parallel to and distal to a second step 100. Alternately, the steps 98, 100 or oriented differently relative to one another. The steps 98, 100 are connected at a transition 102 that may be curved, angled or otherwise configured. The first step 98 is connected to the first tine 92, and the second step 100 is connected to the second tine 94. Before deployment of the staple 90, each step 98, 100 may be substantially perpendicular to the corresponding tine 92, 94 to which it is attached; however, at least one step 98, 100 may be oriented differently. The base 96 and the tines 92, 94 are positioned relative to one another such that the staple 90 is substantially bilaterally symmetrical about an imaginary plane that extends through the base 96 and the tines 92, 94. Alternately, the base 96 and the tines 92, 94 are positioned differently relative to one another. Alternately, the staple 90 is configured differently, and may include additional tines, tines that are shaped differently, a base that is shaped differently, and/or other properties different from the exemplary staple 90 described above.

Advantageously, the staple 90 is a wire staple formed from a single wire, such that the staple 90 is integral. However, the staple 90 may be made from a single piece of material having a different form, such as a sheet of metal. Alternately, the staple 90 is formed from two or more separate components that are connected together in any suitable matter. The staple 90 is metallic, and advantageously is made from stainless steel. Alternately, the staple 90 may be made from nickel-titanium alloy or other metal. Alternately, the staple 90 is made from a nonmetallic material. Alternately, the staple 90 includes a non-metallic coating over a metallic or nonmetallic core or substrate. Alternately, a therapeutic amount of at least one substance is associated with the surface of the staple 90. The staples 90 are oriented in the connection module 12 such that their tines 92, 94 extend substantially distally. The staples 90 may be spaced substantially radially symmetrically relative to the connection module 12. Alternately, the staples 90 are oriented differently relative to the connection module 12.

Figure 9:
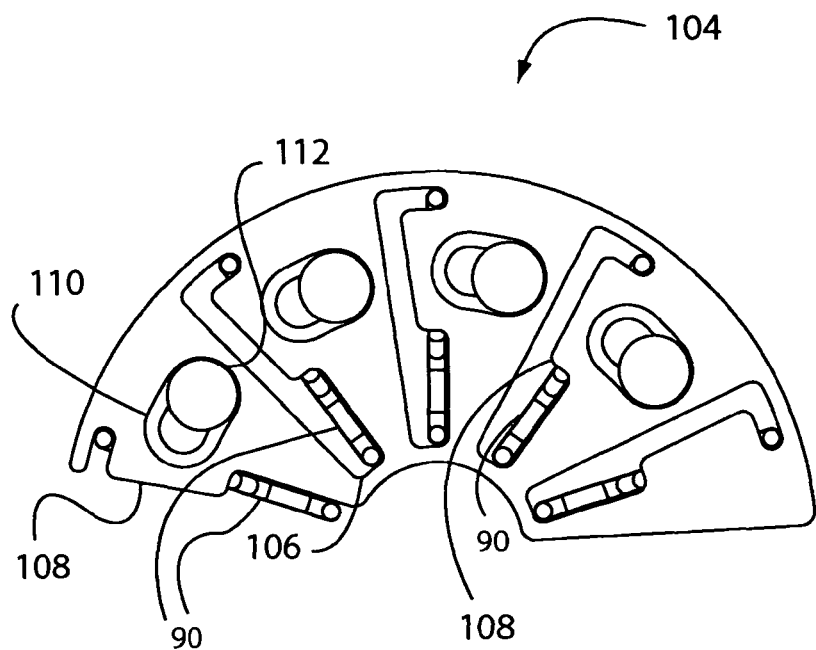
FIG. 9 is a top view of an anvil plate that may be used in conjunction with the connection module, showing the relationship between the anvil plate and connectors.

Referring to FIGS. 6-7 and 9, the connection module 12 includes at least one anvil plate 104. Each anvil plate 104 supports one or more staples 90. Each anvil plate 104 includes at least one aperture 106 defined therein, and at least one anvil 108 that extends into a corresponding aperture 106. Alternately, at least one anvil 108 may be positioned at a different location on the anvil plate 104. Each anvil 108 may be characterized as an external anvil, because it is positioned outside of the tissue to be stapled. Referring also to FIG. 8, the anvil plate 104 may be configured to move between a first position in which it supports at least one staple 90 and a second position in which it frees at least one staple 90. In the first position, each anvil 108 is located distal to and substantially in contact with the first step 98 of a corresponding staple 90. The connection module includes a proximal surface (not shown) located proximal to the first step 98 of each staple 90, such that the first step 98 of each staple 90 is held between the proximal surface and the anvil 108. In the second position, each anvil 108 is no longer located distal to or in contact with the first step 98 of the corresponding staple 90. Thus, in the second position the anvil plate 104 has freed the corresponding staple 90 to exit the connection module 12.

The anvil plate 104 may move from the first position to the second position by rotation, where that rotation is provided by any suitable mechanism. The anvil plate 104 may be actively rotated such as by a shaft or other mechanism. Alternately, the anvil plate 104 may be passively rotated such as by a spring. For example, the spring may bias the anvil plate 104 in a particular direction of rotation, where a structure or mechanism restrains the anvil plate 104 against motion in that direction of rotation until after the staple or staples 90 have been formed. Each anvil plate 104 may include at least one rotation aperture 110, into which a post 112 extends from the connection module. Each rotation aperture 110 acts to limit the rotation of the corresponding anvil plate 104, because contact between each post 112 and an end of the corresponding rotation aperture 110 stops the rotational motion of the anvil plate 104. Alternately, at least one anvil plate 104 is movable between the first position and the second position in a motion other than rotation. At least one post 112 may include a head having a diameter larger than the remainder of the post 112, in order to prevent the anvil plate 104 from moving substantially distally.

Referring to FIGS. 2 and 6-7, the connection module 12 may include a first half 114 and a second half 116 movable relative to one another. Alternately, the connection module 12 includes three or more members relative to one another; the connection module 12 is not limited to having two halves 114, 116. Each half 114, 116 includes at least one anvil plate 104 at or near its distal end, and one or more connectors 90, and is configured to deploy those connectors 90. Alternately, at least one half 114, 116 does not include an anvil plate 104. The halves 114, 116 may be configured similarly, symmetrically or identically to one another for ease of manufacture and/or assembly.

The halves 114, 116 may be movable relative to one another in any suitable manner. For example, an axle 118 may connect the halves 114, 116 to one another, and at least one of the halves 114, 116 may be rotatable about the axle 118. The axle 118 is oriented substantially transverse to the longitudinal axis of the connection module 12, such as at an angle substantially perpendicular to that longitudinal axis or at a different angle relative to that longitudinal axis. Alternately, the axle 118 may be oriented differently relative to the longitudinal axis of the connection module 12. As another example, one or more hinges may be substituted for the axle 118 in order to allow relative rotation of the halves 114, 116. As another example, a living hinge connects the halves 114, 116. As another example, the halves 114, 116 may be slidable relative to one another. As another example, the halves 114, 116 are connected by one or more frangible elements, where application of force to at least one half 114, 116 causes at least one of the frangible elements to break and thereby allows the halves 114, 116 to move relative to one another. As another example, the halves 114, 116 may be connected by one or more mechanical linkages.

Figure 11:
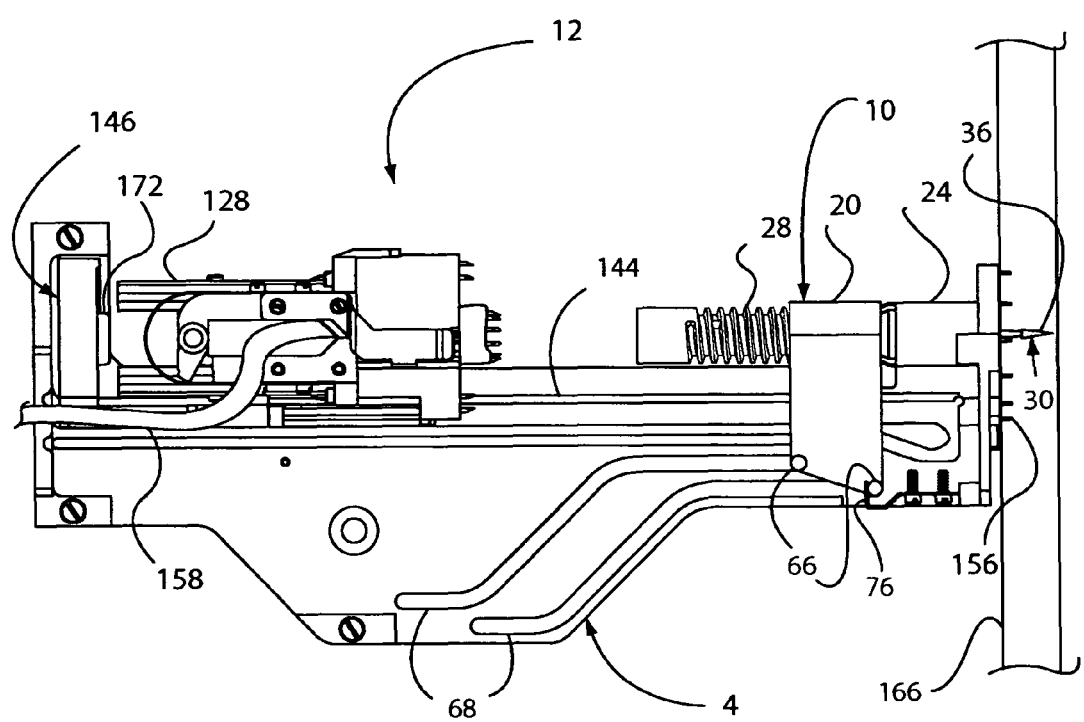
FIG. 11 is a side cutaway view of the effector in an initial configuration.

The halves 114, 116 are movable from a closed position to an open position. Referring also to FIGS. 7 and 11, the connection module 12 may be configured to allow side loading of a graft vessel 120 into the connection module 12. That is, the connection module 12 may be configured to allow one end of the graft vessel 120 to extend out of the connection module 12 at a location lateral to the longitudinal centerline of the connection module 12, rather than through the proximal end of the connection module 12. As one example, at least part of the first half 114 is spaced apart from part of the second half 116 when the connection module 12 is in the closed position in order to form the passage 122 in a side of the connection module 12. Alternately, the connection module 12 is not configured to allow side loading of a graft vessel 120. Each half 114, 116 may include a depression 124 at and/or near its distal end. The depressions 124 may be substantially semicircular in cross section, or may be shaped in a different manner. The depressions 124 may be substantially linear and coaxial with the longitudinal centerline of the connection module 12. Alternately, the depressions 124 may be nonlinear and/or oriented other than coaxially with the longitudinal centerline of the connection module 12. When the connection mechanism 12 is in the closed position, the depressions 124 in the halves 114, 116 are substantially aligned with one another to form a channel 125 for receiving at least a portion of the graft vessel 120. The distal end of each depression 124 may coincide with the distal end of the connection module 12, such that the distal ends of the depressions 124 collectively form an aperture 126 at the distal end of the connection module 12.

Each half 114, 116 includes at least one driver 128. Each driver 128 is movable relative to the corresponding half 114, 116 from a first position to a second position, such as by sliding, or by any other suitable manner. Each driver 128 occupies the first position before deploying one or more corresponding connectors 90, and occupies the second position after deploying one or more corresponding connectors 90. The motion of each driver 128 between the first position and the second position deploys at least one corresponding connector 90, as described in greater detail below. The distal end of at least one driver 128 is the end that contacts one or more corresponding connectors 16, and that distal end is contoured to facilitate deployment of those one or more connectors 16. Each driver 128 may be shaped in any suitable manner. As one example, at least one driver 128 may be an elongated member with a substantially planar proximal end oriented perpendicular to the longitudinal axis of the driver. A plunger (not shown) may be positioned between at least one driver 128 and a corresponding one or more connectors 90, such that the driver 128 urges the plunger distally, and in turn the plunger contacts at least one connector 90.

Referring to FIGS. 2 and 6-7, the connection module 12 may be biased to the open position, such as by at least one spring 130 located at the proximal end of the connection module 12 and connected to both of the halves 114, 116. Where the connection module 12 is biased to the open position, at least one holding member 132 releasably holds the halves 114, 116 in the closed position. As one example, at least one holding member 132 is a leaf spring extending from one of the halves 114, 116 that includes a catch 134 oriented to engage a depression 136 or other feature on the other half 114, 116. The leaf spring 132 is biased at least partially toward the longitudinal axis connection module 12 with sufficient force to hold the catch 134 in the corresponding depression 136 such that the connection module 12 is held in the closed position. Alternately, the connection module 12 is biased to the closed position, and a different structure or mechanism is provided to move the connection module 12 to the open position after it connects the graft vessel to the target vessel. Alternately, the connection module 12 is not biased to the open position or to the closed position.

At least one holding member 132 may include an engagement element 138 extending from it. As one example, the engagement element 138 is positioned at the distal end of the corresponding holding member 132, and extends at least partly in a direction outward from the connection module 12. The frame 14 may be connected to or include at least one stub 140 positioned at or near its distal end, or at a different suitable location. At least one engagement element 138 is pressed into contact with a corresponding stub 140 during the deployment process. This contact, when performed with sufficient force, overcomes the bias of the holding member 132 and moves the holding member 132 outward, thereby moving the catch 134 out of the corresponding depression 136. After the catch 134 has been disengaged from the corresponding depression 136, the connection module 12 can move to the open position, such as under the influence of the spring 130. One or more different or additional structures and/or mechanisms may be provided to provide for the motion of the connection module 12 from the closed position to the open position at the appropriate time in the deployment process.

At least one projection 142 extends from the connection module 12. Advantageously, two or more projections 142 extend laterally from each side of the connection module 12 to provide added stability. The projection or projections 142 may be flanges, pins or any other suitable structures. The projection or projections 142 may extend substantially perpendicular to the longitudinal axis of the connection module 12. Alternately, the projection or projections 142 may extend at a different angle relative to the longitudinal axis of the connection module 12.

The frame 14 includes one or more second grooves 144 defined therein in any suitable manner, such as by molding or machining. The second groove or grooves 144 may extend on the frame 14 at least partially in a different direction than the first grooves 68. Each second groove 144 is configured to receive, and guide the motion of, at least one projection 142. The second groove or grooves 144 form a path along which the projections 142, and thus the connection module 12, travel. Thus, the second groove or grooves 144 may extend along any path or paths that allow for motion of the connection module 12 in a desired manner. As one example, at least one second groove 144 is defined in each side wall 70 of the frame, and the second groove or grooves 144 guide the connection module 12 substantially distally in the direction defined by the original position of the longitudinal axis of the connection module 12. The interaction between each projection 142 and the corresponding second groove 144 may also act to minimize or prevent motion of the connection module 12 in the lateral or vertical directions. Alternately, the connection module 12 includes one or more grooves corresponding to those projections, and the frame 14 has one or more rails, projections or ribs extending therefrom. Alternately, any other or additional appropriate structure or mechanism may be used to guide the motion of the connection module 12.

Optionally, the second groove or grooves 144 may also be used as cable guides. The traveler cable 154 may extend along at least part of the second groove or grooves 144, and may be held in the second groove or grooves 144 by a screw, clip or other mechanism at or near the distal end of the frame 14. Alternately, a separate cable guide may be formed in or connected to the frame 14.

Figure 10:
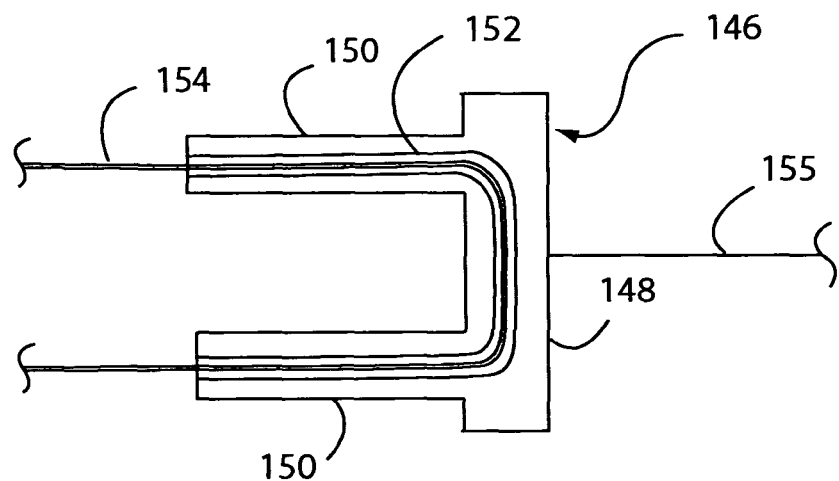
FIG. 10 is a top cross-section view of a traveler.

Referring to FIGS. 2 and 10, a traveler 146 may be located proximal to the connection module 12. The traveler 146 acts to impel the connection module 12 distally during the actuation of the integrated anastomosis tool 2. The traveler 146 includes a plate 148 that may be sized, shaped and configured in any manner that allows distal motion of the plate 148 to impel the connection module 12 distally. For example, the plate 148 may directly contact the connection module 12, such that force applied to the plate 148 in a distal direction impels the connection module 12 distally. At least one leg 150 may extend from the plate 148, such as in the distal direction. At least one leg 150 may extend into, or include a projection that extends into, one of the second grooves 144, such that the traveler 146 follows the same path as the connection module 12 relative to the frame 14. Alternately, at least one leg 150 extends into, or includes a projection that extends into, a groove other than one of the second grooves 144. Alternately, the frame 14 has one or more projections or ribs extending therefrom, and the traveler 146 includes one or more grooves corresponding to those projections. Alternately, any other or additional appropriate structure or mechanism may be used to guide the motion of the traveler 146.

The traveler 146 includes a channel 152 defined therein. The channel 152 may be entirely within the body of the traveler 146, or may be defined entirely or partially on the surface of the traveler 146. The channel 152 is sized and finished to allow a transmission member such as a traveler cable 154 to pass through it. The traveler cable 154 is not fixed to the traveler 146. Rather, the traveler cable 154 enters one end of the channel 152 and extends completely through the channel 152 to exit the other end of the channel 152. The traveler cable 154 is thus free to slide relative to the channel 152. Alternately, the traveler cable 154 or other transmission member is fixed to the traveler 146. A second traveler cable 155 may be attached to the proximal end of the traveler 146 or other part of the traveler 146 in any appropriate manner.

At least one end of the traveler cable 154 extends to the actuator 6. The traveler cable 154 is connected to the actuator 6 such that the application of tension to the traveler cable 154 causes the traveler 146 to move distally and cause the connection module 12 to move distally and deploy connectors to connect the graft vessel to the target vessel. Similarly, at least one end of the cutter cable 46 extends to the actuator 6. The cutter cable 46 may be connected to the actuator 6 such that the application of tension to the cutter cable 46 causes the cutter assembly 10 to move distally, create an opening in the wall of the target vessel, and move out of the way of the connection module 12. The cutter cable 46, the traveler cable 154 and the second traveler cable 155 are collectively one example of a standard interface between the effector 4 and the actuator 6. That is, any actuator 6 configured to apply specific forces to the cables 46, 154, 155 at specific times, as described below, may be utilized, regardless of its structural or mechanical configuration. A different or additional standard interface may be utilized, if desired.

Registration Member

Referring to FIG. 2, at least one registration member 156 may extend from the effector 4, such as from the distal end of the effector 4. The distal end of the effector 4 may be substantially coincident with the distal end of the frame 14. The registration member or members 156 may be spikes 156 that are configured to penetrate the wall of the target vessel at least partially. Alternately, one or more registration members 156 may push down the wall of the target vessel, pull up the wall of the target vessel or otherwise engage the wall of the target vessel without penetrating it while still achieving registration. The cross-sectional area of each spike 156 is selected to be small enough such that the tissue of the target vessel self-closes the aperture created therein by the spike 156 after the spike 156 is removed. Alternately, one or more of the registration members are configured differently. The registration member or members 156 act to hold the effector 4 in a substantially fixed position relative to the opening in the target vessel made by the cutter assembly 10 during actuation of the effector 4. That is, the registration member or members 156 register the distal end of the effector 4 to a particular location on the surface of the target vessel. By registering the effector 4 to the target vessel, the connection module 12 is able to connect the end of the graft vessel 120 to the proper location on the target vessel relative to the opening created by the cutter assembly 10. At least one registration member 156 may extend from an open support 157, which may be crescent-shaped or take any other appropriate shape. The support 157 is open to allow the graft vessel to exit through the open portion after the effector 4 is removed from the anastomosis site, as described below. The support 157 may act as a stop to stop the distal motion of the cutter assembly 10 and/or the connection module 12 during actuation of the effector 4. Alternately, a stop may be provided as a separate structure connected to the support 157. Alternately, an introducer (not shown) such as a sleeve, cage or other mechanism may be used to guide the connection module 12 to the opening created by the cutter assembly 10, thereby registering the connection module 12 to the target vessel. The introducer may be used instead of or in addition to the registration members 156.

Optionally, at least one registration member 156 is configured to test the thickness and/or tissue quality of the wall of the target vessel. As one example, at least one registration member 156 is a hypotube having a sharpened distal end, having at least one orifice near its proximal end that extends to the lumen of the tube. Alternately, the distal end of the hypotube is not sharpened. Alternately, the proximal end of that registration member 156 is open, and no orifice is provided. Such a registration member 156 may be substantially the length of the thickest tissue with which the integrated anastomosis tool 2 may be used. A number of registration members 156 may be provided, each having a different length, such that the thickness of the wall of the target vessel may be determined by viewing the registration members 156 to determine which ones are contacting fluid within the target vessel.

Optionally, the effector 4 includes at least one thickness sensor (not shown) that is separate from the registration member or members 156. For example, an ultrasonic transceiver may be mounted on the effector, where that transceiver is configured to transmit ultrasonic energy to and receive ultrasonic energy from the tissue of the target vessel wall in order to determine its thickness.

Operation

The effector 4 begins in an initial configuration as shown in FIG. 11. In the initial configuration, the cutter assembly 10 is positioned at or near the distal end of the effector 4, and the connector module 12 is positioned proximal to and spaced apart from the cutter assembly 10. When the effector 4 is in the initial configuration, the longitudinal axis of the cutter member 18 is substantially coaxial with the longitudinal axis of the connection module 12. However, the cutter member 18 and the connection module 12 may have a different spatial relationship relative to one another in the initial configuration. For example, the cutter assembly 10 and the connector module 12 may be initially side by side. As another example, the cutter assembly 10 and the connector module 12 may be angled relative to one another such that their longitudinal axes approach one another or intersect at the location on the target vessel where the cutter assembly 10 creates an opening therein.

Graft Vessel Preparation

Referring also to FIGS. 2 and 6-7, the graft vessel is loaded into the connection module 12 while the connection module 12 is in the open position. The graft vessel is placed in the channel 125 of the connection module 12, with a proximal portion of the graft vessel extending through the side of the connection module 12 at the location that will form the passage 122 and a distal portion of the graft vessel extending distal to the distal end of the connection module 12. The connection module 12 is then moved to the closed position, such that a proximal portion of the graft vessel extends out of the passage 122. As described above, a catch 134 on one half 114, 116 may be oriented to engage a depression 136 or other feature on the other half 114, 116. The catch 134 may be connected to a leaf spring 132 that is biased at least partially toward the longitudinal axis of the connection module 12 with sufficient force to hold the catch 134 in the corresponding depression 136 such that the connection module 12 is held in the closed position. The connection module 12 may be outside the effector 4 during the loading process. If so, the connection module 12 is placed into the effector 4 after the graft vessel is loaded, each projections 142 is placed into a second groove 144 as the connector module 12. Alternately, the connection module 12 is connected to the effector 4 in a different manner, such as described above.

Alternately, the graft vessel is loaded into the connection module 12 while the connection module 12 is in the initial, closed configuration. To do so, the graft vessel is pulled through the passage 122 in the side of the connection module 12 and through the channel 125 of the connection module 12. A pull-through tool (not shown) may be utilized to pull the graft vessel through the passage 122 and the channel 125. Such a pull-through tool may be configured in any suitable manner. As one example, the pull-through tool may be substantially as disclosed in co-pending and commonly-assigned U.S. patent application Ser. No. 10/055,179, which is hereby incorporated by reference herein in its entirety. The pull-through tool is flexible enough to be able to extend through the aperture 126 in the distal end of the connection module 12 and bend sufficiently to extend to the edge of or beyond the passage 122. In this way, an end of the pull-through tool engages an end of the graft vessel. Alternately, a surgical forceps or other suitable tool may be used.

The operator then moves the pull-through tool to pull the end of the graft vessel through the passage 122 and through the aperture 126, such that the end of the graft vessel extends distal to the distal ends of the second tines 94 of the connectors 90. The second tines 94 are positioned closer to the longitudinal axis of the connection module 12 than the first tines 92. The end of the graft vessel is then everted over the second tines 94. This eversion may be accomplished in any suitable manner. Alternately, if the first tines 92 are positioned closer to the longitudinal centerline of the connection module 12, the end of the graft vessel is everted over the distal ends of the first tines 92.

Figure 11A:
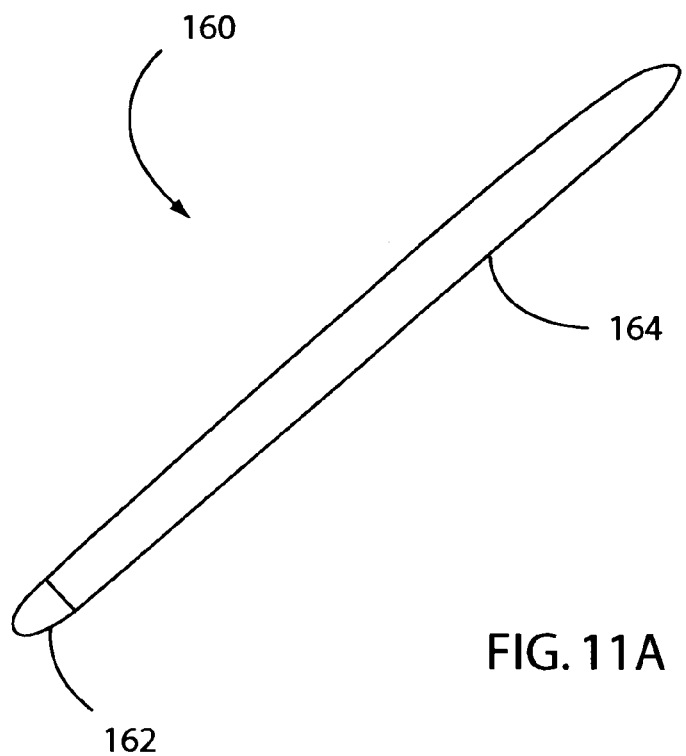
FIG. 11A is a perspective view of an exemplary poke-through tool.
Figure 11B:
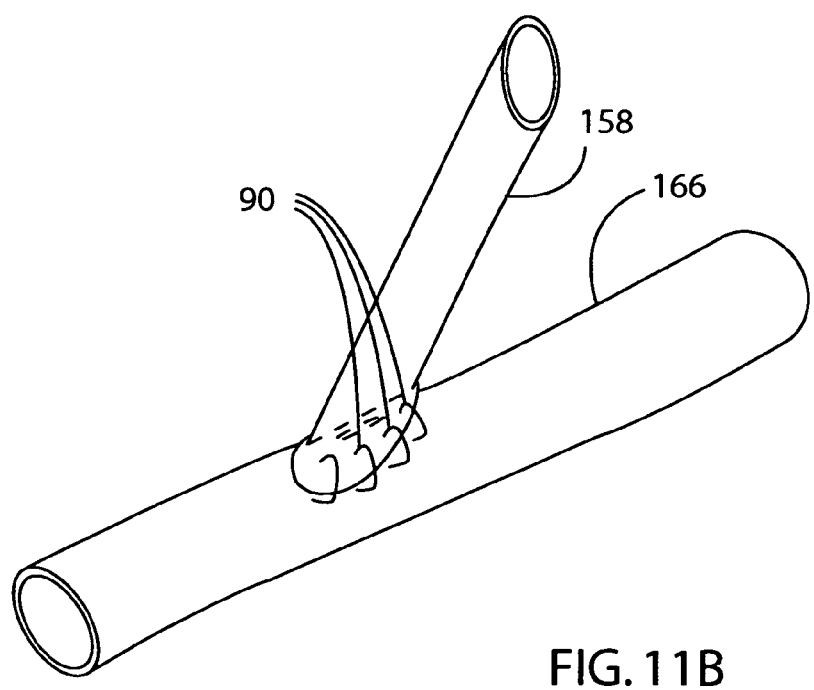
FIG. 11B is a perspective view of an end-to-side anastomosis having a cobrahead configuration.

At least one substantially longitudinal incision may be made in the end of the graft vessel that is pulled through the connection module 12. This incision may be made before or after pull-through. In order to achieve take-off of the graft vessel at an angle to the target vessel, the graft vessel is angled relative to the connection module 12. To facilitate this, a small substantially-longitudinal incision may be made in the distal end of the graft vessel. Further, by providing one incision, a single flap is created at the end of the graft vessel, facilitating the formation of a standard cobrahead anastomosis as shown in FIG. 11B. If so, the graft vessel is oriented relative to the connection module 12 in a manner such that the operator can ensure the cobrahead shape of the finished anastomosis is oriented in a desired manner relative to the target vessel 166. More than one incision may be made, in order to create more than one flap in the end of the graft vessel. By placing the flapped end of the graft vessel at an angle to the end of the connection module 12, where that angle varies based on the width of the graft vessel, the connection module 12 may be used with graft vessels having a variety of widths, while the size of the opening in the target vessel created by the cutter assembly 10 remains the same across graft vessels having different widths. That is, by angling the graft vessel a larger amount relative to the longitudinal axis of the connection module 12, a greater cross-section of the graft vessel is placed adjacent to the opening in the target vessel. Thus, small graft vessels may be angled a greater amount relative to the longitudinal axis of the connection module 12.

In proximity to the apex of this incision, such as above the apex or to the side of the apex, the graft vessel 158 is pierced onto the second tine 94 of a single connector 90. The end of the graft vessel 158 is then everted over the remaining second tines 94 of the remaining connectors 94. Referring also to FIG. 11, the graft vessel 158 is then pushed onto the second tines 94 such that the second tines 94 penetrate the graft vessel 158. The action of pushing the graft vessel 158 onto the second tines 94 may be referred to as "poke-through," and may be performed with a poke-through tool 160 such as shown in FIG. 11A, or a different graft preparation tool. The poke-through tool 160 includes a poke-through tip 162 connected to a handle 164 in any suitable manner. The poke-through tip 162 is composed of a soft material such as rubber or silicone. Alternately, the poke-through tip 162 is substantially rigid and tubular. Alternately, the poke-through tip 162 may be configured in any other suitable manner. The user grasps the handle 164, places the poke-through tip 162 against the everted end of the graft vessel 158, and applies force against the graft vessel 158 toward the distal end of at least one second tine 94. The poke-through tip 162 pushes the tissue of the graft vessel 158 onto the second tine 94, while allowing the distal end of the second tines 94 to penetrate into the soft material of the poke-through tip 162. The poke-through tip 162 is then pulled off of the distal ends of the second tine 94, leaving the everted end of the graft vessel 158 pushed down onto the second tine 94. Advantageously, the material of the poke-through tip 162 is selected and/or treated such that the poke-through tip 162 does not tear, crumble or otherwise substantially degrade as it is pulled off of the second tine or tines 92. The poke-through tip 162 may be sized such that the graft vessel 158 can be pushed onto all of the second tines 94 at one time, or such that the second tines 94 are poked through the graft vessel 158 individually or in separate groups. Alternately, a forceps or other tool or tools is used to poke the second tines 94 through the graft vessel 158, and a separate poke-through tool 160 is not utilized. Alternately, one or more thin pieces of polyester film, standing alone or connected to a mechanism, may be used to poke the second tines 94 through the graft vessel 158.

Selecting an Anastomosis Site

Referring to FIGS. 2 and 11, after the graft vessel 158 has been loaded onto the connection module 12, the operator places the effector 4 on a potential anastomosis site on the target vessel 166. As described above, the interface member 8 may be bent, manipulated or otherwise moved relative to the actuator 6 to facilitate the connection of a graft vessel to a target vessel without the need to hold the actuator 6 in an awkward position. That is, the actuator 6 may be held or otherwise positioned in a desired position, and the effector 4 may then be placed at a potential anastomosis site on the target vessel 166, with the interface member 8 flexing or otherwise moving to accommodate that placement. Where the interface member 8 is flexible, it may be rigidified after the effector 4 has been placed in the desired position. Such rigidification of a flexible member of a surgical tool is standard. Alternately, where the interface member 8 is substantially rigid, or where the effector 4 is directly connected to the actuator 6, the effector 4 may be placed at a potential anastomosis site on the target vessel 166 by moving the actuator 6.

The auger 30 extends distally from the effector 4, and penetrates the wall of the target vessel 166 as the effector 4 is moved in proximity to the target vessel 166. This penetration occurs prior to and separately from the later creation of the opening in the target vessel 166 that allows fluid to pass through the anastomosis. The auger 30 may penetrate the wall of the target vessel 166 partially or completely. After the auger 30 has been inserted through the wall of the target vessel 166, it remains there until the effector 4 is actuated; its presence in the wall of the target vessel 166 maintains hemostasis. As the effector 4 moves into closer proximity with the target vessel 166, the registration member or members 156 then engage the wall of the target vessel 166, penetrating it partially or completely. Alternately, the registration member or members 156 do not penetrate the target vessel wall at all, and instead engage the target vessel wall in a different manner. Motion of the effector 4 toward the target vessel 166 stops when the support 157 or other suitable portion of the effector 4 contacts the wall of the target vessel 166. At this time, the auger 30 has pierced at least the outer surface of the wall of the target vessel 166, and the effector 4 is registered to the potential anastomosis site.

Optionally, the thickness and/or tissue quality of the wall of the target vessel 166 is tested. Where at least one of the registration members 156 is at least partially hollow, that registration member 156 is substantially the length of the thickest tissue with which the integrated anastomosis tool 2 may be used. When the registration member 156 is inserted into the wall of the target vessel 166, and the thickness of the wall is less than the length of the registration member 156, the distal end of the registration member 156 contacts the fluid such as blood that is within the target vessel 166. That fluid enters the hollow interior of the registration member 156 and exits the orifice in the registration member 156 or exits the proximal end of the registration member 156. This allows the operator to observe the outflow and visually confirm that the thickness and quality of the wall of the target vessel 166 is sufficient to proceed. When the registration member 156 is inserted into the wall of the target vessel 166, and the thickness of the wall is greater than the length of the registration member 156 or the interior surface of the wall is calcified, the distal end of the registration member 156 does not contact fluid within the target vessel 166. No fluid exits the orifice or other part of the registration member 156. This allows the operator to observe the lack of outflow and visually confirm that the thickness or quality of the wall of the target vessel 166 is not appropriate, and the operator can then select a different potential location for anastomosis. Where the wall of the target vessel 166 is calcified, the auger 30 will be unable to penetrate completely through the wall due to the presence of the hard calcification, and it will be apparent to the operator that the potential anastomosis site is not suitable even without the use of a thickness-sensing registration member or members 156. Alternately, an ultrasonic transceiver or other mechanism optionally may be used to determine the thickness and/or tissue quality of a candidate anastomosis site.

Creating an Opening in the Target Vessel

After a suitable anastomosis site has been selected on the target vessel 166, and the effector 4 has been registered to that anastomosis site, the user provides any suitable user input to the actuator 6 to actuate it. As one example, the actuator includes a switch, trigger or other mechanism that can be operated by the user with one hand or both hands. As another example, the user input is applied indirectly, such as through an information handling system. The user input may be mechanical, electrical, analog or digital, or any other suitable type of input. The actuator 6 may be mechanically configured in any manner that provides for motion of the cables 46, 154, 155 in the manner described below. For example, the actuator 6 may include a pressurized gas reservoir, or may be connected to a source of pressurized gas. Upon depressing a trigger or otherwise actuating one or more controls, the pressurized gas may be allowed to escape its reservoir into, or otherwise enter, a chamber having a piston (not shown) and exert force on the piston. The piston may be connected directly or indirectly to the cutter cable 46, the traveler cable 154 and/or the second traveler cable 155, which may travel around one or more pulleys (not shown) within the actuator 6.

The cutter assembly 10 is actuated before the connection module 12, to create an opening in the wall of the target vessel 166 before connecting the graft vessel 120 to the target vessel 166. The actuator 6 applies tension to the cutter cable 46, retracting the cutter cable 46 in the proximal direction.

Advantageously, the actuator 6 applies an impulse to the cutter cable 46, thereby actuating the cutter assembly 10 impulsively. As the impulse tensions the cutter cable 46, the cutter cable 46 begins to move proximally.

The cutter cable 46 is wound around at least a portion of the cutter transport 28 proximal to the holder 20, as described above. The cutter cable 46 is thereby offset from the longitudinal centerline of the cutter transport 28, and at least a component of its orientation relative to the cutter transport 28 is substantially tangent to the cutter transport 28. As the cutter cable 46 is tensioned and moved proximally, the tangential component of the force applied by the cutter cable 46 at a location spaced apart from the centerline of the cutter transport 28 causes the cutter transport 28 to rotate. As the cutter cable 46 rotates the cutter transport 28, the angle of the threads 48 on the cutter transport 28 causes the cutter transport 28 to advance distally as it rotates. That is, the cutter transport 28 is threaded in a direction such that the proximal motion of the cutter cable 46 causes the cutter transport 28 to advance distally as it rotates. Rotation begins at substantially the same time as translation. However, rotation or translation may begin first. As the cutter cable 46 continues to be pulled proximally, it is progressively unwound from the cutter transport. The portion of the cutter cable 46 that is wound around at least a portion of the cutter transport 28 proximal to the holder 20 and outside of the bore 22 may remain proximal to the holder 20 and outside of the bore 22 during actuation. Advancement and rotation of the cutter transport causes advancement and rotation of the cutter 24.

Figure 12:
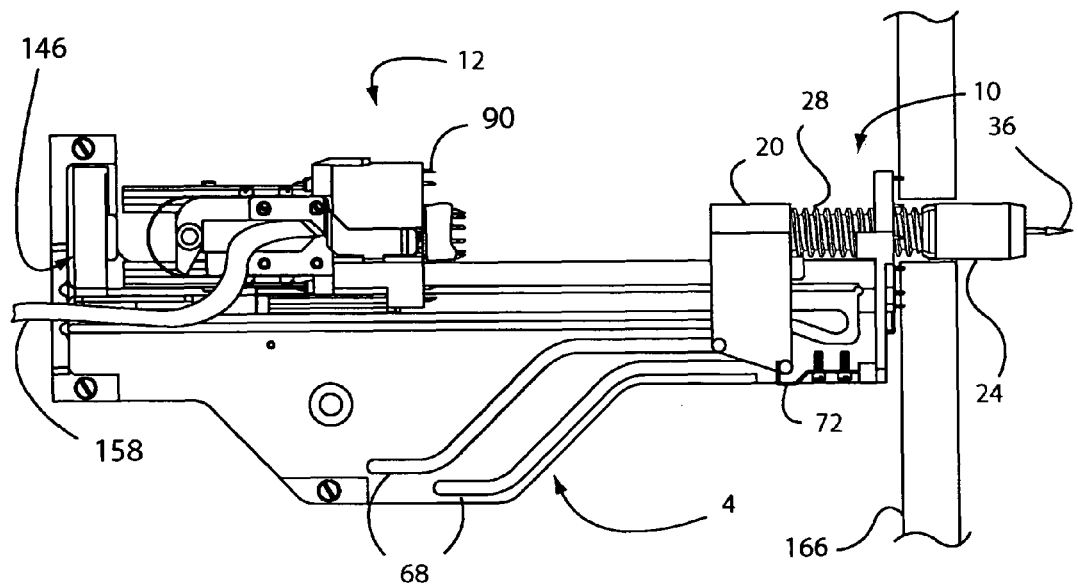
FIG. 12 is a side cutaway view of the effector in a second configuration after the cutter member of the cutter assembly has moved distally.

Referring also to FIG. 12, the cutter 24 advances distally into the wall of the target vessel and cuts the tissue of the wall of the target vessel with both a rotational and translational cutting action. The auger 30 is substantially translationally fixed relative to the cutter 24, such that the auger 30 and the cutter 24 advance distally at substantially the same rate. By constructing the auger 30 and the cutter 24 to be substantially smooth and radially symmetrical, the rotary motion of these structures creates a substantially smooth and clean hole through the wall of the target vessel 166. The tissue of the target vessel 166 may be strain rate sensitive, such as the tissue of the aorta. Strain rate sensitive tissue is easier to cut when the cutting is performed rapidly than when it is performed slowly. By actuating the auger 30 and the cutter 24 impulsively, they move rapidly such that the cutter 24 can better cut strain rate sensitive tissue.

The auger 30 and cutter 24 are advanced into the wall of the target vessel 166 fast enough such that the blood or other fluid in the target vessel 166 acts as a solid and supports the wall of the target vessel 166 against the advance of the piercing member 36 and cutter 24. That is, the auger 30 and cutter 24 advance into the wall of the target vessel 166 fast enough that the fluid within substantially does not have time to move in response to the motion of the auger 30 and cutter 24, such that the fluid acts as if it were a solid. Experiments have shown that the rate at which the auger 30 and cutter 24 should advance to accomplish this effect is at least substantially 0.25 msec. Similarly, the duration over which the cutter transport 28 is advanced is advantageously less than one second; and may be substantially 0.05 seconds. The rotary speed of the cutter 24 is not as critical as the linear speed of the cutter 24 when aortic tissue is to be cut.

The bore 22 in the holder 20 stabilizes the cutter transport 28 while it advances. The length of the bore 22 and its surface finish are selected to provide for such stabilization. The bore 22 also reduces or substantially eliminates precession of the cutter member 18 as it is actuated. Each clip 72 of the effector 4 may hold at least one projection 66 of the holder 20 and substantially restrain that projection 66 against longitudinal motion as the cutter member 18 advances into the wall of the target vessel 166. In this way, the proximal motion of the cutter cable 46 does not simply move the cutter assembly 10 in the proximal direction. The tooth 29 associated with the bore 22 also stabilizes the cutter transport 28 while it advances. By riding between threads 48 of the cutter transport 28 as the cutter transport 28 rotates and advances, the tooth 29 substantially prevents the cutter transport 28 from sliding axially.

After the cutter 24 has penetrated completely through the wall of the target vessel 166, it has cut a tissue plug from that vessel wall to form an opening therein. The cutter 24 cuts a substantially cylindrical tissue plug from the vessel wall due to its tubular shape, thereby leaving a substantially cylindrical opening in the wall of the target vessel 166. The spike 36 is positioned relative to the cutter 24 such that the tissue plug is held within the cutter 24 due to engagement with the ledge 40 of the spike 36 after the tissue plug has been cut. That is, the ledge 40 advances completely through the wall of the target vessel 166 before the cutter 24 has done so, such that the tissue plug cut from the target vessel 166 wall is located proximally to the ledge 40 upon creation of the tissue plug. The ledge 40 is wide enough to reliably hold the tissue plug within the cutter 24. The shaft 38 extends axially through the tissue plug, such that contact between the shaft 38 and the tissue plug acts substantially to prevent radial motion of the tissue plug in the cutter 24. Where a capture feature or features are provided on the cutter 24 itself, they may engage the tissue plug instead of or in addition to the ledge 40. Alternately, the ledge 40 is omitted, and friction holds the tissue plug in the cutter 24.

The distal translation of the cutter 24 and auger 30 continues through a fixed distance greater than the thickness of the vessel wall, to ensure that the cutter 24 has completely penetrated the wall of the target vessel 166. That fixed distance is selected to be greater than the maximum tissue thickness with which the effector 4 is to be used, but lesser than the interior diameter of the target vessel 166. The rotation of the cutter transport 28, and hence the cutter member 18 as a whole, substantially stops when the cutter cable 46 has been pulled proximally far enough such that no cutter cable 46 remains on the cutter transport 28 to be unwound. Alternately, a clutch or other mechanism may be provided to allow the cutter transport 28 to continue rotating for a short time after creating an opening in the target vessel 166, thereby dissipating at least some energy associated with its angular momentum. That is, the cutter transport 28 may be allowed to idle rotationally after it has completed its distal translation. Alternately, the cutter transport 28 encounters a stop (not shown) that substantially stops distal motion of the cutter transport 28 while allowing the cutter cable 46 to move proximally. The stop may extend from or be connected to the frame 14. Alternately, the stop is the tooth 29 in the holder 20. When the holder 20 has moved to its most distal location and has stopped its motion, and the cutter transport 28 has rotated such that the tooth 29 encounters the most proximal thread 48, the tooth 29 acts as a stop.

The cutter transport 28 and the length of the cutter cable 46 are selected such that the opening in the wall of the target vessel 166 has been created before the time at which no more cutter cable 46 remains to be unwound from the cutter transport 28. The distal end of the cutter cable 46 is fixed to the cutter transport 28, such as at the anchor feature 50. Thus, when no more cutter cable 46 remains to be unwound from the cutter transport 28, further proximal motion of the cutter cable 46 no longer acts substantially tangentially to the cutter transport 28, but substantially longitudinally to the cutter transport 28. In this way, a single cable 46 can be utilized to actuate the cutter assembly 10, move it out of the opening in the target vessel 166, and move the cutter assembly 10 out of the way of the connection module 12. Optionally, one or more additional cables may be provided.

As the cutter member 18 moves proximally, the cutter 24 moves proximally. The shoulder 43 of the cutter 24 encounters the holder 20 as the cutter member 18 moves proximally. The shoulder 43 extends beyond the diameter of the bore 22 such that it does not pass through the bore 22, but rather engages the distal surface of the holder 20. This engagement exerts a proximal force on the holder 20. In this way, the cutter cable 46 exerts a retraction force on the cutter assembly 10 in the proximal direction. The retraction force is larger than the proximal force experienced by the cutter assembly 10 during rotation of the cutter transport 28. The clip or clips 72 are constructed such that the clip or clips 72, taken together, resist an amount of force in the proximal direction that is less than that amount of retraction force but greater than the proximal force experienced by the cutter assembly 10 during rotation of the cutter transport 28. The force exerted by the cutter cable 46 thereby overcomes the force exerted by each clip 72 on the corresponding projection 66, causing the clip or clips 72 to flex out of the way of the projection or projections 66 and allowing the cutter assembly 10 to move proximally past the clip or clips 72.

Figure 13:
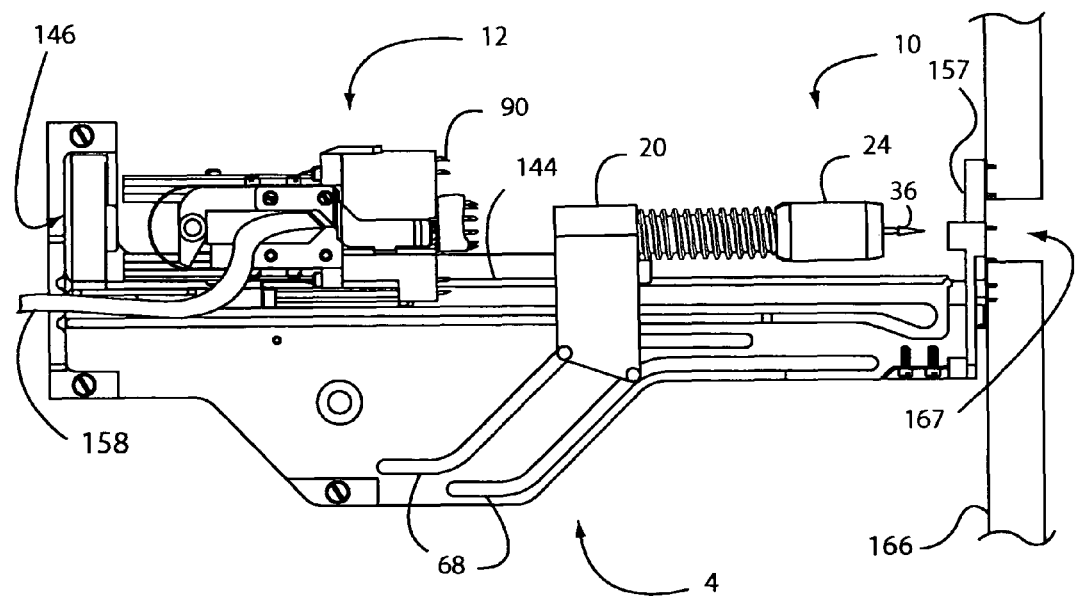
FIG. 13 is a side cutaway view of the effector in a third configuration after the cutter assembly has moved proximally after creating an opening in the target vessel.

Referring also to FIG. 13, as the cutter assembly 10 moves proximally, the cutter 24 moves out of the opening 167 that it created in the wall of the target vessel 166, and removes the tissue plug from the opening 167. The tissue plug is held within the cutter 24 by friction with the inner surface of the cutter 24 and/or by contact with the ledge 40 of the auger 30. The cutter assembly 10 thus has created an opening through the wall of the target vessel 166 at a location that had been previously substantially intact. In this way, where the target vessel 166 carries blood, the cutter assembly 10 disrupts the hemostasis of the target vessel 166 at the location where the cutter assembly 10 enters tissue. Alternately, the cutter assembly 10 may be used to make a larger opening in the wall of the target vessel 166 at a location where an opening already exists.

Figure 14:
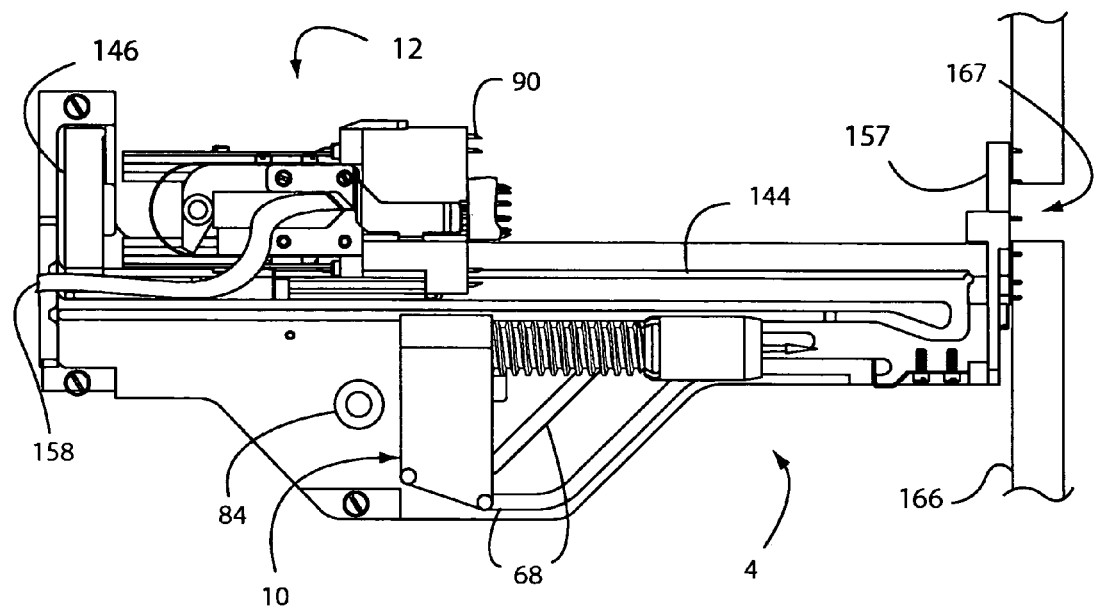
FIG. 14 is a side cutaway view of the effector in a fourth configuration after the cutter assembly has moved off-axis.

Each projection 66 extending from the holder 20 is received and guided by at least one first groove 68. As the cutter assembly 10 moves proximally, it follows the path of the first groove or grooves 68 in the frame 14. Referring also to FIG. 2, the first grooves 68 extend substantially longitudinally at the distal end of the frame 14, such that the cutter assembly 10 is moved substantially in the proximal direction after it has created an opening 167 in the wall of the target vessel 166. The first groove or grooves 68 extend along the frame 14 in such a manner as to move the cutter assembly 10 off-axis as it is moved proximally. That is, the first groove or grooves 68 extend along a path that provides for motion of the cutter assembly 10 away from the line defined by the original position of the longitudinal centerline of the cutter member 18. As an example, starting at the distal end of the frame 14, the first groove or grooves 68 extend substantially longitudinally, then angle partially away from the longitudinal direction, then continue to extend substantially longitudinally before stopping. Referring also to FIG. 14, as the cutter assembly 10 continues to move proximally under the influence of the cutter cable 46, the cutter assembly 10 moves off-axis along the path defined by the first groove or grooves 68, then moves longitudinally again. When the most-proximal projection 66 of the holder 20 encounters the proximal end 168 of the corresponding first groove 68, that contact stops the proximal motion of the cutter assembly 10 in a final position. Continued tension in the cutter cable 46 maintains the cutter assembly 10 in that final position during the remainder of the operation of the effector 4. Alternately, tension on the cutter cable 46 is released at least in part, and friction or interference between at least one of the projections 66 and the proximal end 168 of the corresponding first groove 68 holds the cutter assembly 10 in the final position. Alternately, tension on the cutter cable 46 is released at least in part, and a catch or other mechanism engages at least one projection 66 or a different part of the cutter assembly 10 and holds the cutter assembly 10 in the final position. Alternately, the proximal motion of the cutter assembly 10 is stopped in a different manner.

Connecting the Graft Vessel to the Target Vessel

With the cutter assembly 10 moved off-axis, the path is clear for the connection module 12 to advance distally. The connection module 12 may begin its distal travel before or after the cutter assembly 10 has moved off-axis, as long as the timing of their relative motion is such that they do not collide with one another. Referring also to FIG. 10, the connection module 12 may be moved distally by applying tension to the traveler cable 154. Both proximal ends of the traveler cable 154 are retracted proximally to do so. As both proximal ends of the traveler cable 154 are retracted proximally, the portion of the traveler cable 154 proximal to the cable guide 84 is pulled distally, because the cable guide 84 reverses the direction of the traveler cable 154. As a result, the portion of the traveler cable 154 within the channel 152 in the traveler 146 is pulled distally, which in turn causes the traveler 146 to move distally. As the traveler 146 moves distally, it pushes the connection module 12 distally. Alternately, one proximal end of the traveler cable 154 is substantially fixed, and only the other proximal end is moved proximally. Referring also to FIG. 6, each projection 142 extending from the connection module 12 is received and guided by at least one second groove 144. Further, each leg 150 of the traveler 146 is received and guided by at least one second groove 144 or other groove substantially parallel to the second groove 144. The second groove or grooves 144 are substantially longitudinal, and are oriented on the frame 14 to translate the connection module 12 substantially longitudinally to the distal end of the effector 4. Alternately, the second groove or grooves are curved or otherwise shaped, and convey the connection module 12 to the distal end of the effector 4. Alternately, the cutter assembly 10 and the connection module 12 can be moved in any manner and in any direction that allows each of them to perform its function.

Figure 15:
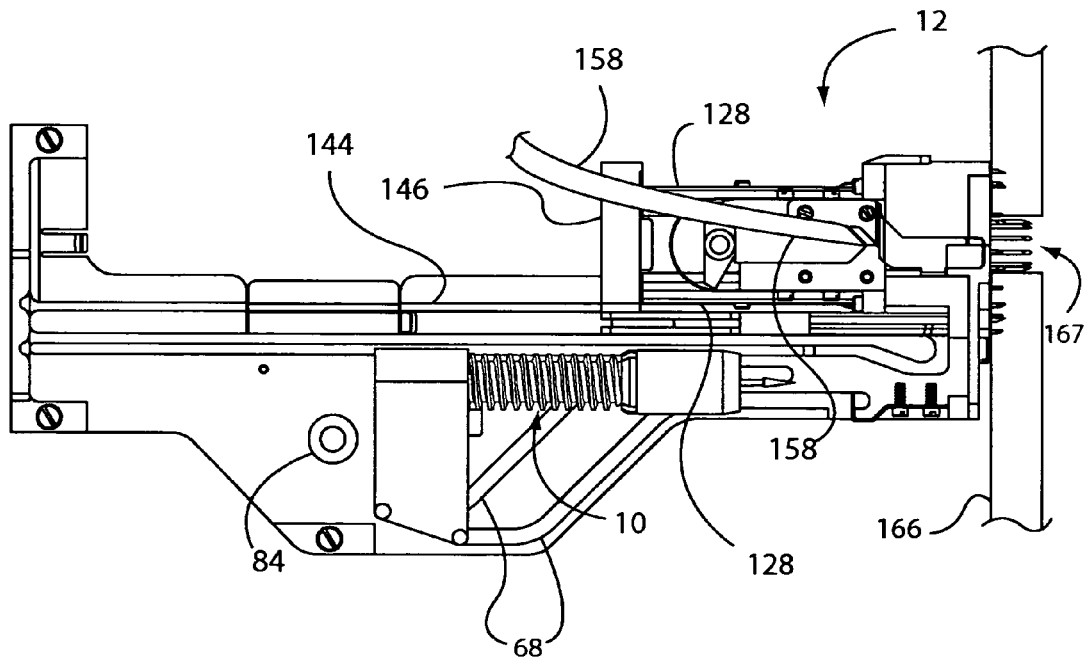
FIG. 15 is a side cutaway view of the effector in a fifth configuration after the connection module has shuttled distally.
Figure 16:
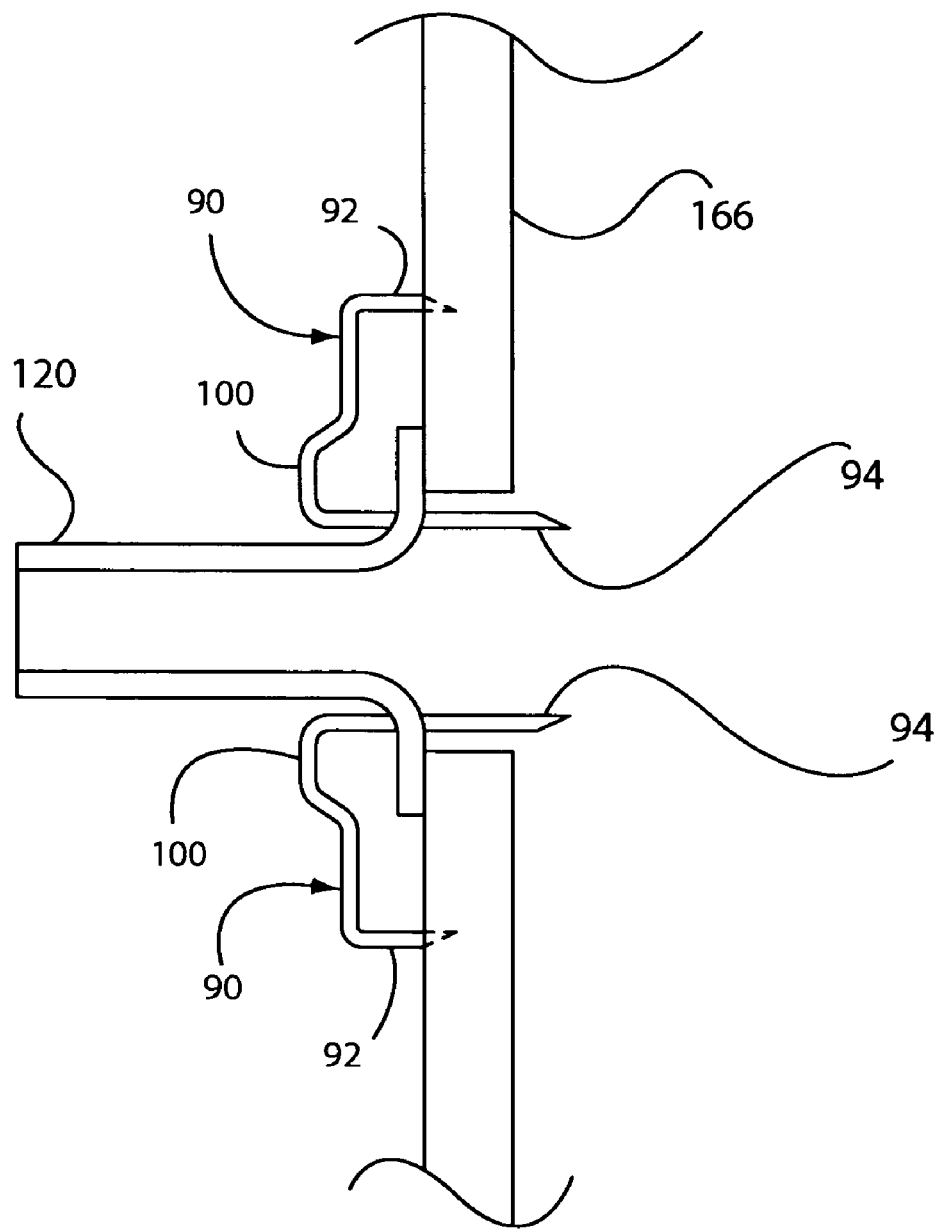
FIG. 16 is a side cross-section view of tines of connectors entering the opening in the target vessel with the graft vessel everted over those tines, as the connection module moves distally to the position of FIG. 15.

Referring also to FIG. 15, as the connection module 12 is pushed distally by the traveler 146, the connection module 12 approaches the stop 170 at the distal end of the effector 4. Where the connectors 90 are staples 90, the longer second tine 94 of each staple moves past the distal end of the effector 4 and enters the opening 167 in the target vessel 166 wall created by the cutter assembly 10. Alternately, where the connectors 90 are not staples, any suitable portion of one or more connectors 90 may enter the opening 167 in the wall of the target vessel 166 as the connection module 12 approaches the stop 170. Referring also to FIG. 16, an end of the graft vessel 120 was previously everted over the second tines 94 and pushed down on them, as described above. As the connection module 12 approaches the stop, where the connector 90 is a staple 90, the first tine 92 of each staple 90 penetrates the wall of the target vessel 166, partially or completely. This penetration occurs in proximity to the opening 167 in the target vessel 166, such that the first tines 92 are spaced apart from one another in tissue around the opening 167.

The traveler 146 continues to push the connection module 12 distally until the connection module 12 encounters the stop 170. The stop 170 is sized and shaped to prevent the connection module 12 from moving substantially further in the distal direction after the connection module 12 encounters it. When the connection module 12 stops, the everted end of the graft vessel 120 is in contact with, or close to contact with, the outer surface of the wall of the target vessel 166.

Figure 17:
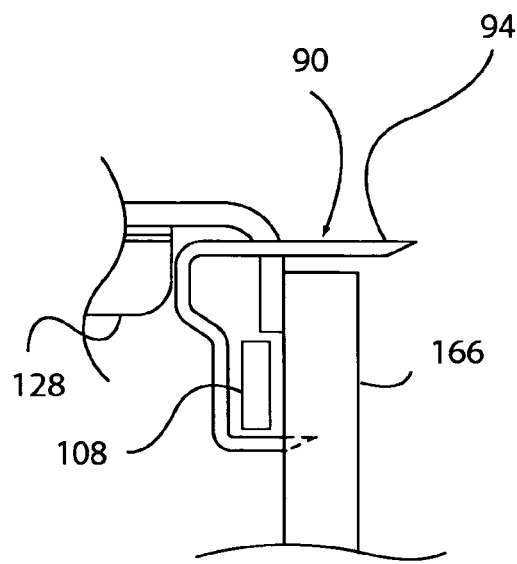
FIG. 17 is a side cross-section view of a connector positioned in the target vessel after the connection module has moved to the position of FIG. 15, prior to deployment.

After the connection module 12 has stopped, tension is still applied to the traveler cable 154. The traveler 146 cannot urge the connection module 12 any further distally due to interference by the stop 170. As a result, referring also to FIGS. 6-7, the traveler 146 applies force in the distal direction to the drivers 128. The drivers 128 are initially biased away from the connectors 90 with a force less than is applied by the traveler 146 after the connection module 12 has encountered the stop 170. After the connection module 12 encounters the stop 170, the distal force applied by the traveler 146 to the drivers 128 overcomes that bias and urges the drivers 128 distally toward the connectors 90. Referring also to FIG. 17, each driver 128 moves distally toward at least one corresponding connector 90 or a plunger interposed between the driver 128 and the connector 90. Referring also to FIG. 9, where the connectors 90 are stepped staples 90 as described above, the first step 98 of each staple 90 is positioned proximal to a corresponding anvil 108 on one of the anvil plates 104. The first step 98 is closer to the first tine 92 of each staple 90. As each driver 128 moves distally, it contacts the second step 100 of at least one corresponding staple 90. This motion of the driver 128 exerts a force on the second step 100, and thereby a moment about the anvil 108. As a result, each staple 90 begins to bend. The bending may be concentrated at the transition 102 between the steps 98, 100 of each staple 90. Alternately, the bending may be distributed across a greater portion of at least one staple 90, or may be concentrated in a different part of at least one staple 90.

Figure 18:
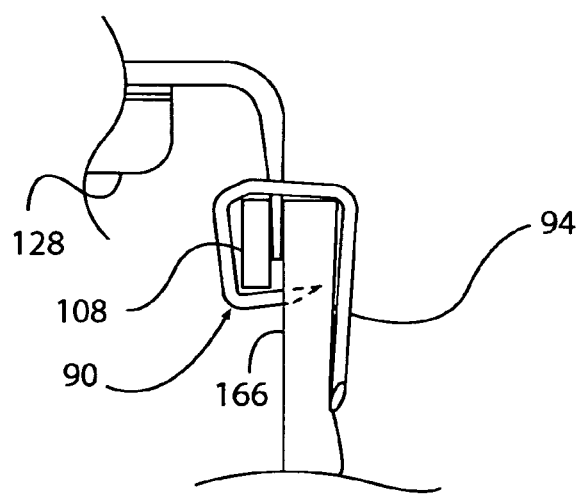
FIG. 18 is a side cross-section view of a connector positioned in the target vessel after the connection module has moved to the position of FIG. 15, after deployment.

Referring also to FIG. 18, as each driver 128 moves distally against the second step 100 of one or more staples 90, each staple 90 deforms such that its second tine 94 bends outward and proximally, coming to rest against the inner surface of the wall of the target vessel 166 without substantially penetrating it. Thus, the first tine 92 of each staple 90 penetrates at least the outer surface of the wall of the target vessel 166, and the second tine 94 of each staple 90 does not substantially penetrate the inner surface of the wall of the target vessel 166. Alternately, the first tine 92 and/or second tine 94 of at least one staple 90 may have a different relationship with the wall of the target vessel 166 after deployment. After the staples 90 have been deployed, the tissue at the distal end of the graft vessel 120 that had been everted over the second tines 94 shifts such that the inner surface of the end of the graft vessel 120 is placed in contact with the outer surface of the wall of the target vessel 166. Such a connection may be referred to as a cobrahead. However, the topology of the anastomosis may be different, if desired. In the deployed configuration, the staples 90 hold and control the edge of the opening 167 in the target vessel 166, and hold the end of the graft vessel 120 against the outer surface of the target vessel 166. The anastomosis between the end of the graft vessel 120 and the side of the target vessel 166 is thus complete.

The cutter assembly 10 advantageously is moved off-axis rapidly after creating the opening 167 in the target vessel 166. Further, the actuation of the traveler 146 to move the connection module 12 distally and deploy the connectors 90 advantageously is performed rapidly. An impulsive force may be applied to the cutter assembly 10 and to the traveler 146 to cause such rapid motion. Such rapid motion of the cutter assembly 10 and the connection module 12 provides virtual hemostasis. As used in this document, "virtual hemostasis" refers to limiting blood loss through the opening 167 in the target vessel 166 by minimizing the period of time between the cutting and connecting operations. As one example of virtual hemostasis, where the target vessel 166 is the aorta and the heart is beating, the time between the creation of the opening 167 in the wall of the target vessel 166 and the deployment of the connectors 90 to connect the graft vessel 120 to the target vessel 166 is less than one second, such that a minimal amount of blood escapes through the opening 167. Further, the term "quick shuttle" may be used to refer to motion of the cutter assembly 10 and the connection module 12 within a short period of time to provide virtual hemostasis.

After the connectors 90 have been deployed and the anastomosis has been completed, each anvil plate 104 is rotated relative to the corresponding half 114, 116 of the connection module 12. The anvil plate or plates 104 may be rotated by any suitable structure, mechanism or method. The rotation of each anvil plate 104 moves each anvil 108 laterally relative to the corresponding staple 90, such that each anvil 108 is no longer distal to the base 96 of the corresponding staple 90. In this way, the staples 90 are freed from the anvils 108 and free to move out of the connection module 12 via the corresponding aperture 106 in the anvil plate 104, and the connection module 12 is free to move proximally away from the deployed connectors 90 and the target vessel 166.

Figure 19:
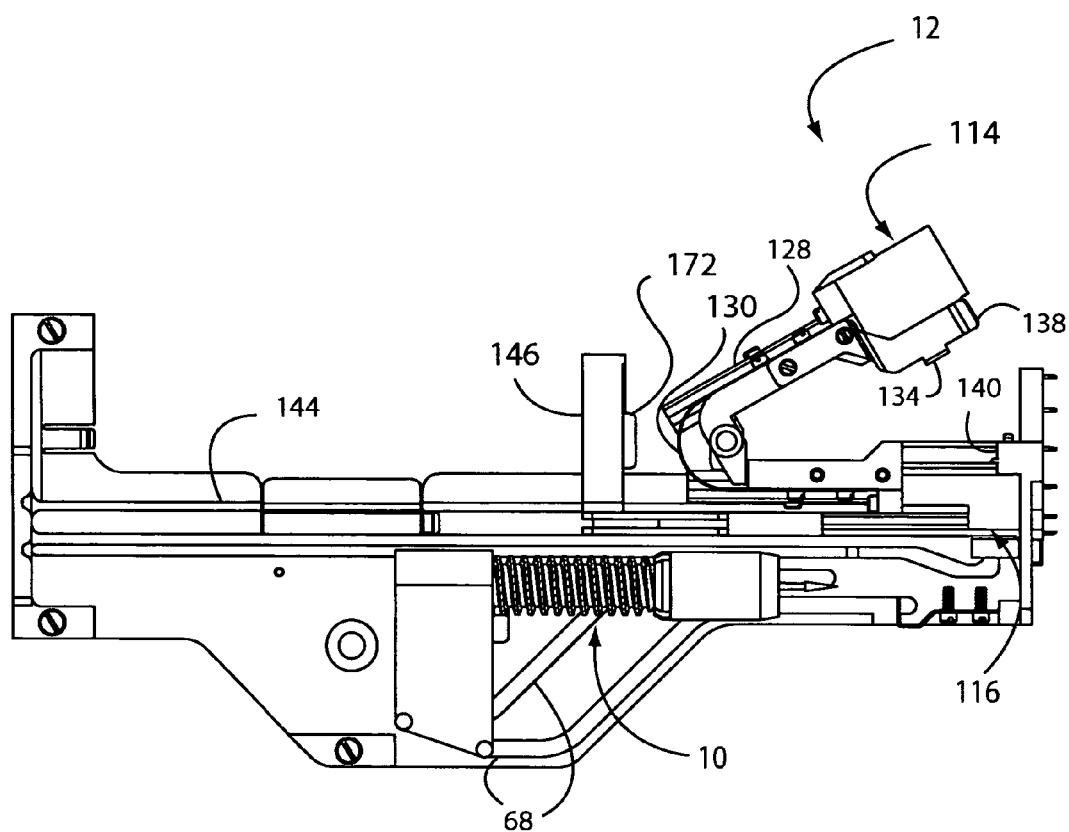
FIG. 19 is a side cutaway view of the effector in a sixth configuration after the connection module has deployed connectors to connect the graft vessel to the target vessel and has opened to release the graft vessel.

As the traveler cable 154 continues to force the traveler 146 distally, the engagement element 138 of each leaf spring 132 on the connector module 12 is forced against the corresponding stub 140 at the distal end of the frame 14. As a result, the distal end of each leaf spring 132 is pushed away from the longitudinal axis of the connection module 12. As each leaf spring 132 is forced away from the longitudinal centerline of the connection module 12, this motion causes the catch 134 on each leaf spring 132 to move out of the corresponding depression 136 in the other half 114, 116 of the connection module 12. As a result, the catch 134 no longer holds the connection module 12 in the closed position. The second traveler cable 155 is then moved proximally, pulling the traveler 146 away from the connection module 12. The spring 130 then biases at least the distal ends of the halves 114, 116 apart from one another, opening the connection module 12 to the open position shown in FIGS. 6 and 19. Because the traveler 146 has moved away from the connection module 12, the halves 114, 116 are free to move to the open position. Alternately, the second traveler cable 155 is not provided, and the traveler 146 is otherwise configured to allow the connection module 12 to open while the traveler 146 is in contact with it.

Optionally, the traveler 146 includes a shelf 172 defined in the distal surface of the plate 148. As the traveler 146 moves distally, the proximal end of at least one driver 128 engages the distal surface of the plate 148, and the shelf 172 is positioned adjacent to a portion of that driver 128 near its proximal end. The shelf 172 prevents the connection module 12 from moving to an open position, because the shelf 172 would interfere with at least one driver 128 if the connection module 12 were to attempt to open. However, after the drivers 128 have been driven distally to deploy the connectors 90, they are positioned distal to the shelf 172, such that interference with the shelf 172 no longer prevents the connection module 12 from moving to the open position. Thus, the shelf 172 acts as a safety to ensure that the connection module 12 opens at the appropriate time. Alternately, the shelf 172 is used instead of the leaf spring or springs 134 to hold the connection module 12 in the closed position until the appropriate time for it to open.

The effector 4 is then moved away from the target vessel 166, such that the registration member or members 156 move away from the target vessel 166. Where the registration member or members 156 are a spike or spikes, the cross-sectional area of each spike is small enough that the aperture created by each spike in the wall of the target vessel 166 closes as that spike is removed. In this way, substantially no leakage from the target vessel 166 results from the removal of the registration member or members 156.

The effector 4 is then moved laterally relative to the graft vessel 120. With the connection module 12 open, the graft vessel 120 may exit the connection module 12 through the side thereof. The support 157 at the distal end of the effector 4 is open as well, to allow the graft vessel 120 to exit from the side of the connection module 12 and through the open portion of the support 157. Providing for the side exit of the graft vessel 120 from the effector 4 allows for flexibility in the performance of surgical procedures such as CABG. For example, where the graft vessel 120 is side-loaded into the connection module 12 and is capable of exiting from the side of the connection module 12, and the integrated anastomosis tool 2 is used to perform a proximal anastomosis between a graft vessel 120 and the aorta, the proximal anastomosis can be performed before or after the distal anastomosis between the graft vessel 120 and a coronary artery. This flexibility may be particularly useful where the integrated anastomosis tool 2 is used in the performance of an endoscopic or minimally-invasive CABG procedure, and/or where a mammary artery or other artery is used for anastomosis such that no proximal anastomosis is necessary.

Proximal/Distal Anastomoses

The effector 4 can be utilized to perform an anastomosis between the end of any tubular tissue structure and the side of any tubular tissue structure. As an example, the effector 4 may be used to perform a proximal anastomosis between a graft vessel and the aorta in a CABG procedure. As another example, the effector 4 may be used to perform a distal anastomosis between a graft vessel and a coronary artery in a CABG procedure. The effector 4 is particularly well suited to distal anastomosis in a beating-heart CABG procedure, due to its ability to provide virtual hemostasis; the heart does not substantially move in the very short duration between making an opening in the coronary artery and deploying connectors to connect the graft vessel to the coronary artery.

Where the effector 4 is used for distal anastomosis between a graft vessel and a coronary artery, the cutter assembly 10 may be configured differently. For example, the cutter assembly 10 may simply be a sharp edge that is actuated to move out of the distal end of the effector 4, create a substantially linear slit in the coronary artery, then retract back into the effector 4 and move off-axis. The sharp edge may move solely in the longitudinal direction relative to the effector 4, or may move along at least part of the length of the coronary artery. Alternately, the cutter assembly 10 may be modified in any other suitable manner to facilitate its use with for distal anastomosis.

In addition, where the effector 4 is used for distal anastomosis, the connectors 90 may be scaled down in size relative to the connectors 90 utilized for proximal anastomosis, or different connectors 90 may be used for distal anastomosis than for proximal anastomosis.

While the invention has been described in detail, it will be apparent to one skilled in the art that various changes and modifications can be made and equivalents employed, without departing from the present invention. For example, the system described above may be used for surgical procedures other than CABG procedures, such as peripheral vascular surgery, neurovascular surgery, or transplant surgery. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A surgical apparatus for connecting a graft vessel to a target vessel, comprising:
    an actuator; and
    an effector operationally connected to said actuator, said effector configured to place the graft vessel in fluid communication with the target vessel; wherein said effector comprises a frame, a cutter assembly movably connected to said frame and a connection module connected to said frame, wherein said connection module is movable between an open position and a closed position, and wherein at least part of said connection module is rotatable about a first axis to move between said open position and said closed position;
    wherein said cutter assembly includes a rotatable cutter having a generally circular cutting edge at the distal end thereof, whereby rotation of said cutter creates an opening in the wall of the target vessel, and wherein said cutter assembly is movable from a first position on said frame in which said cutter is substantially in axial alignment with the longitudinal centerline of the opening to a second position on said frame in which said cutter is substantially out of axial alignment with the longitudinal centerline of the opening, wherein said cutter assembly is connected to said frame in both said first position and said second position and wherein said first position and said second position are separated from one another on said frame; wherein said frame remains substantially stationary adjacent the opening in the wall of the target vessel during motion of said cutter assembly from said first position to said second position; and
    wherein said connection module includes an anvil plate and a plurality of independent connectors held by said anvil plate, wherein said cutter assembly is moveable along said frame to said second position before said connection module deploys said connectors; and wherein said connectors are deformable against said anvil plate, after which said anvil plate is rotatable about a second axis relative to a remainder of said connection module to free said connectors, wherein said second axis is different from said first axis.

2. The surgical apparatus of claim 1, further comprising an interface member connected to said actuator and to said effector, wherein at least a portion of said interface member is bendable.

3. The surgical apparatus of claim 2, wherein said bendable portion of said interface member is at least partially flexible.

4. The surgical apparatus of claim 1, further comprising an interface member connected to said actuator and to said effector, wherein at least a portion of said interface member is at least partially articulated.

5. The surgical apparatus of claim 1, further comprising at least one registration member extending from said effector.

6. The surgical apparatus of claim 1, further comprising at least one thickness sensor connected to said effector.

7. The surgical apparatus of claim 1, wherein said cutter assembly and said connection module are independently actuatable.

8. The surgical apparatus of claim 1, further comprising a cable connected to said cutter assembly and to said actuator, wherein application of force to said cable actuates said cutter assembly.

9. The surgical apparatus of claim 1, wherein said actuator is configured to apply an impulsive force to at least one of said cutter assembly and said connection module.

10. The surgical apparatus of claim 1, wherein said connection module includes an aperture defined therein to permit side loading of the graft vessel.

11. The surgical apparatus of claim 1, wherein said axis is angled relative to the longitudinal centerline of said connection module.

12. The surgical apparatus of claim 1, wherein at least one of said connectors is a staple.

13. The surgical apparatus of claim 1, wherein at least one of said connectors is a clip.

14. The surgical apparatus of claim 1, wherein said frame comprises grooves defined therein, and wherein said cutter assembly includes at least one projection extending therefrom, each of said projections movable within at least one of said grooves, wherein said cutter assembly slides along at least one said groove from said first position to said second position.

15. The surgical apparatus of claim 1, wherein said frame comprises rails extending therefrom, and wherein said cutter assembly grooves therein, each of said grooves movable along at least one of said rails, wherein said cutter assembly slides along at least one said rail from said first position to said second position.

16. The surgical apparatus of claim 1, wherein said cutter assembly includes an auger at its distal end, wherein said auger is substantially translationally fixed relative to said cutter.

17. The surgical apparatus of claim 16, wherein said auger is a spike.

18. The surgical apparatus of claim 16, wherein said cutter assembly includes a cutter transport connected to said cutter, wherein said cutter is located distal to said cutter transport.

19. The surgical apparatus of claim 18, wherein at least part of said cutter transport is threaded.

20. The surgical apparatus of claim 18, further comprising a cutter cable wound around at least part of the threaded cutter transport, said cutter cable also connected to said actuator.

21. The surgical apparatus of claim 1, wherein the longitudinal centerline of said cutter in said first position is substantially parallel to and spaced apart from said longitudinal centerline of said cutter in said second position.

22. The surgical apparatus of claim 1, wherein said cutter assembly moves from said first position to said second position at least in part along a direction angled relative to the longitudinal centerline of said cutter in said first position.

* * * * *